(12) United States Patent
Adamek-Bowers et al.

(10) Patent No.: US 12,053,371 B2
(45) Date of Patent: Aug. 6, 2024

(54) PROSTHETIC VALVE DELIVERY SYSTEM

(71) Applicant: SHIFAMED HOLDINGS, LLC, Campbell, CA (US)

(72) Inventors: Jasper Adamek-Bowers, San Francisco, CA (US); Noah Goldsmith, Santa Cruz, CA (US); Jordan Skaro, San Jose, CA (US); Jonathan Oakden, San Jose, CA (US); Claudio Argento, Felton, CA (US); Uyenchi Ha, San Jose, CA (US); Andrew Backus, Santa Cruz, CA (US)

(73) Assignee: Shifamed Holdings, LLC, Campbell, CA (US)

( * ) Notice: Subject to any disclaimer, the term of this patent is extended or adjusted under 35 U.S.C. 154(b) by 0 days.

(21) Appl. No.: 18/043,458

(22) PCT Filed: Aug. 31, 2021

(86) PCT No.: PCT/US2021/048472
§ 371 (c)(1),
(2) Date: Feb. 28, 2023

(87) PCT Pub. No.: WO2022/047393
PCT Pub. Date: Mar. 3, 2022

(65) Prior Publication Data
US 2023/0310147 A1   Oct. 5, 2023

Related U.S. Application Data

(60) Provisional application No. 63/072,788, filed on Aug. 31, 2020.

(51) Int. Cl.
*A61F 2/24* (2006.01)

(52) U.S. Cl.
CPC .......... *A61F 2/2409* (2013.01); *A61F 2/2457* (2013.01); *A61F 2210/0014* (2013.01)

(58) Field of Classification Search
CPC .... A61F 2/2466; A61F 2/2454; A61F 2/2451; A61F 2/2418; A61F 2/2457; A61F 2/2409; A61F 2210/0014; A61M 25/0147
See application file for complete search history.

(56) References Cited

U.S. PATENT DOCUMENTS

| | | |
|---|---|---|
| 4,725,274 A | 2/1988 | Lane et al. |
| 5,002,563 A | 3/1991 | Pyka et al. |

(Continued)

FOREIGN PATENT DOCUMENTS

| | | |
|---|---|---|
| AU | 2012261727 B2 | 10/2015 |
| AU | 2019246822 B2 | 8/2020 |

(Continued)

OTHER PUBLICATIONS

Schaefer; Large heart valves—small heart valves; ISMAAP; Oct. 19, 2015; 5 pages; retrieved from the internet (https://www.ismaap.org/condition-detail/large-heart-valves-small-heart-valves/) on Mar. 21, 2023.

(Continued)

*Primary Examiner* — Erich G Herbermann
(74) *Attorney, Agent, or Firm* — Shay Glenn LLP

(57) ABSTRACT

A delivery system for delivering a spiral anchor to a diseased native valve of a heart includes an anchor control catheter and an anchor guide extending from the anchor control catheter. The anchor guide includes a flexible configuration and a rigid configuration. The anchor guide in the rigid configuration includes a proximal section, a middle section, and a distal section. The proximal section includes a straight central axis and extends from the anchor control catheter, the middle section spirals axially and radially outwards from the (Continued)

central axis, and the distal section curves concentrically about the central axis in a plane that is perpendicular to the central axis.

10 Claims, 34 Drawing Sheets

(56) References Cited

U.S. PATENT DOCUMENTS

| | | |
|---|---|---|
| 5,327,905 A | 7/1994 | Avitall |
| 5,356,424 A | 10/1994 | Buzerak et al. |
| 5,370,685 A | 12/1994 | Stevens |
| 5,582,616 A | 12/1996 | Bolduc et al. |
| 5,755,601 A | 5/1998 | Jones |
| 5,779,669 A | 7/1998 | Haissaguerre et al. |
| 5,873,835 A | 2/1999 | Hastings et al. |
| 5,944,690 A | 8/1999 | Falwell et al. |
| 5,997,526 A | 12/1999 | Giba et al. |
| 6,048,339 A | 4/2000 | Zirps et al. |
| 6,053,873 A | 4/2000 | Govari et al. |
| 6,254,550 B1 | 7/2001 | McNamara et al. |
| 6,419,695 B1 | 7/2002 | Gabbay |
| 6,419,696 B1 | 7/2002 | Ortiz et al. |
| 6,530,952 B2 | 3/2003 | Vesely |
| 6,533,783 B1 | 3/2003 | Töllner |
| 6,641,553 B1 | 11/2003 | Chee et al. |
| 6,752,813 B2 | 6/2004 | Goldfarb et al. |
| 6,908,478 B2 | 6/2005 | Alferness et al. |
| 6,964,684 B2 | 11/2005 | Ortiz et al. |
| 6,974,476 B2 | 12/2005 | McGuckin, Jr. et al. |
| 7,077,861 B2 | 7/2006 | Spence |
| 7,101,395 B2 | 9/2006 | Tremulis et al. |
| 7,125,421 B2 | 10/2006 | Tremulis et al. |
| 7,160,322 B2 | 1/2007 | Gabbay |
| 7,175,656 B2 | 2/2007 | Khairkhahan |
| 7,201,771 B2 | 4/2007 | Lane |
| 7,226,467 B2 | 6/2007 | Lucatero et al. |
| 7,381,219 B2 | 1/2008 | Salahieh et al. |
| 7,329,279 B2 | 2/2008 | Haug et al. |
| 7,445,631 B2 | 11/2008 | Salahieh et al. |
| 7,470,285 B2 | 12/2008 | Nugent et al. |
| 7,527,647 B2 | 5/2009 | Spence |
| 7,534,261 B2 | 5/2009 | Freidman |
| 7,563,267 B2 | 7/2009 | Goldfarb et al. |
| 7,594,903 B2 | 9/2009 | Webler et al. |
| 7,604,646 B2 | 10/2009 | Goldfarb et al. |
| 7,608,091 B2 | 10/2009 | Goldfarb et al. |
| 7,618,449 B2 | 11/2009 | Tremulis et al. |
| 7,621,948 B2 | 11/2009 | Herrmann et al. |
| 7,666,204 B2 | 2/2010 | Thornton et al. |
| 7,704,269 B2 | 4/2010 | St. Goar et al. |
| 7,731,705 B2 | 6/2010 | Wardle |
| 7,748,389 B2 | 7/2010 | Salahich et al. |
| 7,749,266 B2 | 7/2010 | Forster et al. |
| 7,780,725 B2 | 8/2010 | Haug et al. |
| 7,799,069 B2 | 9/2010 | Bailey et al. |
| 7,811,296 B2 | 10/2010 | Goldfarb et al. |
| 7,824,442 B2 | 11/2010 | Salahieh et al. |
| 7,824,443 B2 | 11/2010 | Salahieh et al. |
| 7,846,203 B2 | 12/2010 | Cribier |
| 7,947,075 B2 | 5/2011 | Goetz et al. |
| 7,951,195 B2 | 5/2011 | Antonsson et al. |
| 7,959,666 B2 | 6/2011 | Salahleh et al. |
| 7,988,724 B2 | 8/2011 | Salahieh et al. |
| 8,021,421 B2 | 9/2011 | Fogarty et al. |
| 8,052,749 B2 | 11/2011 | Salahieh et al. |
| 8,052,750 B2 | 11/2011 | Tuval et al. |
| 8,062,355 B2 | 11/2011 | Figulla et al. |
| 8,070,800 B2 | 12/2011 | Lock et al. |
| 8,075,615 B2 | 12/2011 | Eberhardt et al. |
| 8,096,985 B2 | 1/2012 | Legaspi et al. |
| 8,147,541 B2 | 4/2012 | Forster et al. |
| 8,147,542 B2 | 4/2012 | Maisano et al. |
| 8,182,528 B2 | 5/2012 | Salahieh et al. |
| 8,216,256 B2 | 7/2012 | Raschdorf et al. |
| 8,236,049 B2 | 8/2012 | Rowe et al. |
| 8,241,351 B2 | 8/2012 | Cabiri |
| 8,251,977 B2 | 8/2012 | Partlett |
| 8,252,050 B2 | 8/2012 | Maisano et al. |
| 8,287,584 B2 | 10/2012 | Salahleh et al. |
| 8,313,526 B2 | 11/2012 | Hoffman et al. |
| 8,323,241 B2 | 12/2012 | Salahleh et al. |
| 8,323,336 B2 | 12/2012 | Hill et al. |
| 8,328,868 B2 | 12/2012 | Paul et al. |
| 8,343,213 B2 | 1/2013 | Salahieh et al. |
| 8,348,995 B2 | 1/2013 | Tuval et al. |
| 8,348,996 B2 | 1/2013 | Tuval et al. |
| 8,366,767 B2 | 2/2013 | Zhang |
| 8,403,981 B2 | 3/2013 | Forster et al. |
| 8,403,983 B2 | 3/2013 | Quadri et al. |
| 8,414,643 B2 | 4/2013 | Tuval et al. |
| 8,414,644 B2 | 4/2013 | Quadri et al. |
| 8,414,645 B2 | 4/2013 | Dwork et al. |
| 8,425,593 B2 | 4/2013 | Braido et al. |
| 8,449,599 B2 | 5/2013 | Chau et al. |
| 8,454,686 B2 | 6/2013 | Alkhatib |
| 8,465,541 B2 | 6/2013 | Dwork |
| 8,500,800 B2 | 8/2013 | Maisano et al. |
| 8,512,401 B2 | 8/2013 | Murray et al. |
| 8,523,881 B2 | 9/2013 | Cabiri et al. |
| 8,545,553 B2 | 10/2013 | Zipory et al. |
| 8,556,963 B2 | 10/2013 | Tremulis et al. |
| 8,562,645 B2 | 10/2013 | Stone et al. |
| 8,562,673 B2 | 10/2013 | Yeung et al. |
| 8,579,962 B2 | 11/2013 | Salahieh et al. |
| 8,603,157 B2 | 12/2013 | Seguin et al. |
| 8,603,160 B2 | 12/2013 | Salahieh et al. |
| 8,623,075 B2 | 1/2014 | Murray et al. |
| 8,628,570 B2 | 1/2014 | Seguin |
| 8,641,727 B2 | 2/2014 | Starksen et al. |
| 8,652,202 B2 | 2/2014 | Alon et al. |
| 8,652,203 B2 | 2/2014 | Quadri et al. |
| 8,657,872 B2 | 2/2014 | Seguin |
| 8,685,086 B2 | 4/2014 | Navia et al. |
| 8,696,693 B2 | 4/2014 | Najafi et al. |
| 8,715,342 B2 | 5/2014 | Zipory et al. |
| 8,740,976 B2 | 6/2014 | Tran et al. |
| 8,784,479 B2 | 7/2014 | Antonsson et al. |
| 8,790,367 B2 | 7/2014 | Nguyen et al. |
| 8,808,368 B2 | 8/2014 | Maisano et al. |
| 8,828,078 B2 | 9/2014 | Salahich et al. |
| 8,834,564 B2 | 9/2014 | Tuval et al. |
| 8,840,663 B2 | 9/2014 | Salahieh et al. |
| 8,840,664 B2 | 9/2014 | Karapetian et al. |
| 8,845,588 B2 | 9/2014 | Bruszewski |
| 8,852,271 B2 | 10/2014 | Murray et al. |
| 8,876,893 B2 | 11/2014 | Dwork et al. |
| 8,876,894 B2 | 11/2014 | Tuval et al. |
| 8,876,895 B2 | 11/2014 | Tuval et al. |
| 8,900,294 B2 | 12/2014 | Paniagua et al. |
| 8,911,494 B2 | 12/2014 | Hammer et al. |
| 8,920,369 B2 | 12/2014 | Salahieh et al. |
| 8,926,690 B2 | 1/2015 | Kowalsky |
| 8,926,696 B2 | 1/2015 | Cabiri et al. |
| 8,926,697 B2 | 1/2015 | Gross et al. |
| 8,940,002 B2 | 1/2015 | Goertzen |
| 8,940,044 B2 | 1/2015 | Hammer et al. |
| 8,951,299 B2 | 2/2015 | Paul et al. |
| 8,986,371 B2 | 3/2015 | Quill et al. |
| 8,998,980 B2 | 4/2015 | Shipley et al. |
| 9,005,273 B2 | 4/2015 | Salahleh et al. |
| 9,011,515 B2 | 4/2015 | Schweich et al. |
| 9,011,523 B2 | 4/2015 | Seguin |
| 9,011,530 B2 | 4/2015 | Reich et al. |
| 9,017,408 B2 | 4/2015 | Siegal et al. |
| 9,023,100 B2 | 5/2015 | Quadri et al. |
| 9,034,032 B2 | 5/2015 | McLean et al. |
| 9,039,757 B2 | 5/2015 | McLean et al. |
| 9,056,009 B2 | 6/2015 | Keränen |
| 9,061,120 B2 | 6/2015 | Osypka et al. |
| 9,095,431 B2 | 8/2015 | Yu et al. |
| 9,119,719 B2 | 9/2015 | Zipory et al. |
| 9,125,739 B2 | 9/2015 | Paniagua et al. |
| 9,125,740 B2 | 9/2015 | Morriss et al. |

(56) References Cited

U.S. PATENT DOCUMENTS

| | | |
|---|---|---|
| 9,155,619 B2 | 10/2015 | Liu et al. |
| 9,168,129 B2 | 10/2015 | Valdez et al. |
| 9,168,131 B2 | 10/2015 | Yohanan et al. |
| 9,173,713 B2 | 11/2015 | Hart et al. |
| 9,173,737 B2 | 11/2015 | Hill et al. |
| 9,180,006 B2 | 11/2015 | Keränen |
| 9,226,823 B2 | 1/2016 | Dwork |
| 9,232,995 B2 | 1/2016 | Kovalsky et al. |
| 9,277,994 B2 | 3/2016 | Miller et al. |
| 9,289,297 B2 | 3/2016 | Wilson et al. |
| 9,295,547 B2 | 3/2016 | Costello et al. |
| 9,301,756 B2 | 4/2016 | Wardle |
| 9,301,836 B2 | 4/2016 | Buchbinder et al. |
| 9,320,597 B2 | 4/2016 | Savage et al. |
| 9,343,224 B2 | 5/2016 | Zilbershlag |
| 9,358,110 B2 | 6/2016 | Paul et al. |
| 9,414,915 B2 | 8/2016 | Lombardi et al. |
| 9,427,315 B2 | 8/2016 | Schweich et al. |
| 9,439,757 B2 | 9/2016 | Wallace et al. |
| 9,468,525 B2 | 10/2016 | Kovalsky |
| 9,474,606 B2 | 10/2016 | Zipory et al. |
| 9,474,840 B2 | 10/2016 | Siess |
| 9,480,559 B2 | 11/2016 | Vidlund et al. |
| 9,492,273 B2 | 11/2016 | Wallace et al. |
| 9,526,487 B2 | 12/2016 | Rahmani |
| 9,526,609 B2 | 12/2016 | Salahieh et al. |
| 9,532,868 B2 | 1/2017 | Braido |
| 9,532,870 B2 | 1/2017 | Cooper et al. |
| 9,561,102 B2 | 2/2017 | Rust et al. |
| 9,579,198 B2 | 2/2017 | Deem et al. |
| 9,636,224 B2 | 5/2017 | Zipory et al. |
| 9,636,481 B2 | 5/2017 | Campbell et al. |
| 9,662,202 B2 | 5/2017 | Quill et al. |
| 9,662,206 B2 | 5/2017 | Börtlein et al. |
| 9,662,209 B2 | 5/2017 | Gross et al. |
| 9,675,454 B2 | 6/2017 | Vidlund et al. |
| 9,681,952 B2 | 6/2017 | Hacohen et al. |
| 9,687,343 B2 | 6/2017 | Börtlein et al. |
| 9,724,192 B2 | 8/2017 | Sheps et al. |
| 9,730,790 B2 | 8/2017 | Quadri et al. |
| 9,730,793 B2 | 8/2017 | Reich et al. |
| 9,744,031 B2 | 8/2017 | Girard et al. |
| 9,744,038 B2 | 8/2017 | Dahlgren et al. |
| 9,750,605 B2 | 9/2017 | Ganesan et al. |
| 9,763,779 B2 | 9/2017 | Börtlein et al. |
| 9,763,780 B2 | 9/2017 | Morriss et al. |
| 9,814,611 B2 | 11/2017 | Cartledge et al. |
| 9,827,090 B2 | 11/2017 | Hill et al. |
| 9,861,480 B2 | 1/2018 | Zakai et al. |
| 9,867,700 B2 | 1/2018 | Bakis et al. |
| 9,867,702 B2 | 1/2018 | Keränen et al. |
| 9,877,833 B1 | 1/2018 | Bishop et al. |
| 9,883,941 B2 | 2/2018 | Hastings et al. |
| 9,889,003 B2 | 2/2018 | Börtlein et al. |
| 9,895,221 B2 | 2/2018 | Vidlund |
| 9,895,222 B2 | 2/2018 | Zeng et al. |
| 9,901,444 B2 | 2/2018 | Valdez et al. |
| 9,918,840 B2 | 3/2018 | Reich et al. |
| D815,744 S | 4/2018 | Ratz et al. |
| 9,949,825 B2 | 4/2018 | Braido et al. |
| 9,949,828 B2 | 4/2018 | Sheps et al. |
| 9,950,142 B2 | 4/2018 | Eversull et al. |
| 9,968,452 B2 | 5/2018 | Sheps et al. |
| 9,974,647 B2 | 5/2018 | Ganesan et al. |
| 9,974,650 B2 | 5/2018 | Nguyen-Thien-Nhon et al. |
| 9,999,504 B2 | 6/2018 | Cyyscon et al. |
| 10,004,599 B2 | 6/2018 | Rabito et al. |
| 10,016,271 B2 | 7/2018 | Morriss et al. |
| 10,016,272 B2 | 7/2018 | Spence et al. |
| 10,028,832 B2 | 7/2018 | Quill et al. |
| 10,029,037 B2 | 7/2018 | Muller et al. |
| 10,034,747 B2 | 7/2018 | Harewood |
| 10,034,749 B2 | 7/2018 | Spence et al. |
| 10,039,637 B2 | 8/2018 | Maimon et al. |
| 10,045,846 B2 | 8/2018 | Bonyuet et al. |
| 10,052,198 B2 | 8/2018 | Chau et al. |
| 10,052,199 B2 | 8/2018 | Spence et al. |
| 10,058,318 B2 | 8/2018 | Tegzes |
| 10,058,321 B2 | 8/2018 | Sampson et al. |
| 10,064,719 B2 | 9/2018 | Börtlein et al. |
| 10,070,954 B2 | 9/2018 | Braido et al. |
| 10,092,400 B2 | 10/2018 | Jimenez et al. |
| 10,098,734 B2 | 10/2018 | Hoang |
| 10,105,217 B2 | 10/2018 | Keränen |
| 10,105,224 B2 | 10/2018 | Buchbinder et al. |
| 10,130,464 B2 | 11/2018 | Meiri et al. |
| 10,130,471 B2 | 11/2018 | Keränen et al. |
| 10,143,552 B2 | 12/2018 | Wallace et al. |
| 10,149,759 B2 | 12/2018 | Naor |
| 10,172,708 B2 | 1/2019 | Anderson |
| 10,172,711 B2 | 1/2019 | Keränen |
| 10,179,042 B2 | 1/2019 | Braido et al. |
| 10,195,021 B2 | 2/2019 | Keränen et al. |
| 10,195,025 B2 | 2/2019 | Levi et al. |
| 10,195,027 B2 | 2/2019 | Nasr |
| 10,195,028 B2 | 2/2019 | Hosmer et al. |
| 10,195,029 B2 | 2/2019 | Keränen |
| 10,201,418 B2 | 2/2019 | Biadillah et al. |
| 10,206,775 B2 | 2/2019 | Kovalsky et al. |
| 10,213,307 B2 | 2/2019 | Dwork et al. |
| 10,226,330 B2 | 3/2019 | Spence et al. |
| 10,226,334 B2 | 3/2019 | Rowe et al. |
| 10,238,489 B2 | 3/2019 | Conklin |
| 10,251,749 B2 | 4/2019 | Zerkowski et al. |
| 10,258,464 B2 | 4/2019 | Delaloye et al. |
| 10,258,468 B2 | 4/2019 | Deem et al. |
| 10,265,169 B2 | 4/2019 | Desrosiers et al. |
| 10,271,950 B2 | 4/2019 | Neustadter |
| 10,299,917 B2 | 5/2019 | Morriss et al. |
| 10,299,921 B2 | 5/2019 | Dale et al. |
| 10,314,701 B2 | 6/2019 | Von Segesser et al. |
| 10,321,988 B2 | 6/2019 | Gorman et al. |
| 10,321,989 B2 | 6/2019 | Keränen |
| 10,327,743 B2 | 6/2019 | St. Goar et al. |
| 10,327,766 B2 | 6/2019 | Zerkowski et al. |
| 10,335,277 B2 | 7/2019 | Crisostomo et al. |
| 10,338,724 B2 | 7/2019 | Zhao |
| 10,350,066 B2 | 7/2019 | Cooper et al. |
| 10,357,351 B2 | 7/2019 | Cooper et al. |
| 10,357,634 B2 | 7/2019 | Simmons et al. |
| 10,363,130 B2 | 7/2019 | Armer et al. |
| 10,363,131 B2 | 7/2019 | Eidenschink et al. |
| 10,368,986 B2 | 8/2019 | Gosal et al. |
| 10,368,990 B2 | 8/2019 | Noe et al. |
| 10,376,266 B2 | 8/2019 | Herman et al. |
| 10,376,360 B2 | 8/2019 | Bruchman et al. |
| 10,376,363 B2 | 8/2019 | Quadri et al. |
| 10,398,547 B2 | 9/2019 | Li et al. |
| 10,426,608 B2 | 10/2019 | Salahieh et al. |
| 10,433,961 B2 | 10/2019 | McLean |
| 10,470,881 B2 | 11/2019 | Noe et al. |
| 10,478,291 B2 | 11/2019 | Nguyen et al. |
| 10,500,048 B2 | 12/2019 | Khairkhahan et al. |
| 10,507,104 B2 | 12/2019 | Zhang et al. |
| 10,512,541 B2 | 12/2019 | Zerkowski et al. |
| 10,524,901 B2 | 1/2020 | Quadri et al. |
| 10,548,729 B2 | 2/2020 | Zipory et al. |
| 10,568,737 B2 | 2/2020 | Noe et al. |
| 10,575,951 B2 | 3/2020 | Johnson et al. |
| 10,603,165 B2 | 3/2020 | Maimon et al. |
| 10,639,154 B2 | 5/2020 | Seguin |
| 10,653,524 B2 | 5/2020 | Khairkhahan et al. |
| 10,660,753 B2 | 5/2020 | Pham et al. |
| 10,687,938 B2 | 6/2020 | Patel et al. |
| 10,695,160 B2 | 6/2020 | Lashinski et al. |
| 10,702,386 B2 | 7/2020 | Khairkhahan et al. |
| 10,709,552 B2 | 7/2020 | Backus et al. |
| 10,716,662 B2 | 7/2020 | Delaloye et al. |
| 10,722,352 B2 | 7/2020 | Spence |
| 10,722,353 B2 | 7/2020 | Levi |
| 10,729,542 B2 | 8/2020 | Howard et al. |
| 10,743,991 B2 | 8/2020 | Brown |
| 10,751,180 B2 | 8/2020 | Schewel |
| 10,751,184 B2 | 8/2020 | Reich et al. |

(56) References Cited

U.S. PATENT DOCUMENTS

| | | |
|---|---|---|
| 10,765,514 B2 | 9/2020 | Iflah et al. |
| 10,813,749 B2 | 10/2020 | Nguyen et al. |
| 10,828,153 B2 | 11/2020 | Noe et al. |
| 10,856,970 B2 | 12/2020 | Tuval et al. |
| 10,869,755 B2 | 12/2020 | Granada et al. |
| 10,888,420 B2 | 1/2021 | Bateman et al. |
| 10,912,644 B2 | 2/2021 | Argento et al. |
| 10,973,629 B2 | 4/2021 | Levi et al. |
| 10,973,630 B2 | 4/2021 | Torrianni et al. |
| 11,007,057 B2 | 5/2021 | Pham et al. |
| 11,020,221 B2 | 6/2021 | Arcaro et al. |
| 11,039,922 B2 | 6/2021 | Konno |
| 11,471,282 B2 | 10/2022 | Argento et al. |
| 11,672,657 B2 | 6/2023 | Argento et al. |
| 2002/0173841 A1 | 11/2002 | Ortiz et al. |
| 2003/0114913 A1 | 6/2003 | Spenser et al. |
| 2003/0233142 A1 | 12/2003 | Morales et al. |
| 2004/0039442 A1 | 2/2004 | St. Goar et al. |
| 2004/0044350 A1 | 3/2004 | Martin et al. |
| 2005/0137686 A1 | 6/2005 | Salahieh et al. |
| 2005/0137687 A1 | 6/2005 | Salahich et al. |
| 2005/0137691 A1 | 6/2005 | Salahieh et al. |
| 2005/0137694 A1 | 6/2005 | Haug et al. |
| 2005/0137696 A1 | 6/2005 | Salahleh et al. |
| 2005/0165344 A1 | 7/2005 | Dobak, III |
| 2005/0240202 A1 | 10/2005 | Shennib et al. |
| 2005/0277839 A1 | 12/2005 | Alderman et al. |
| 2006/0009841 A1 | 1/2006 | McGuckin, Jr. et al. |
| 2006/0052821 A1 | 3/2006 | Abbot et al. |
| 2006/0074484 A1 | 4/2006 | Huber |
| 2006/0178700 A1 | 8/2006 | Quinn |
| 2006/0217762 A1 | 9/2006 | Maahs et al. |
| 2006/0259136 A1 | 11/2006 | Nguyen et al. |
| 2006/0293698 A1 | 12/2006 | Douk |
| 2007/0051377 A1 | 3/2007 | Douk et al. |
| 2007/0055206 A1 | 3/2007 | To et al. |
| 2007/0118151 A1 | 5/2007 | Davidson |
| 2007/0142907 A1 | 6/2007 | Moaddeb et al. |
| 2007/0185572 A1 | 8/2007 | Solem et al. |
| 2007/0255396 A1 | 11/2007 | Douk et al. |
| 2007/0293724 A1 | 12/2007 | Saadat et al. |
| 2007/0293943 A1 | 12/2007 | Quinn |
| 2008/0004696 A1 | 1/2008 | Vesely |
| 2008/0004697 A1 | 1/2008 | Lichtenstein et al. |
| 2008/0200980 A1 | 8/2008 | Robin et al. |
| 2008/0208327 A1 | 8/2008 | Rowe |
| 2008/0275503 A1 | 11/2008 | Spence et al. |
| 2008/0275540 A1 | 11/2008 | Wen |
| 2009/0093826 A1 | 4/2009 | Warder-Gabaldon |
| 2009/0138079 A1 | 5/2009 | Tuval et al. |
| 2009/0192601 A1 | 7/2009 | Rafiee et al. |
| 2009/0209950 A1 | 8/2009 | Starksen |
| 2009/0222026 A1 | 9/2009 | Rothstein et al. |
| 2009/0276040 A1 | 11/2009 | Rowe et al. |
| 2010/0010520 A1 | 1/2010 | Takahashi et al. |
| 2010/0049239 A1 | 2/2010 | McGuckin, Jr. et al. |
| 2010/0076497 A1 | 3/2010 | Zwirkoski |
| 2010/0094406 A1 | 4/2010 | Leprince et al. |
| 2010/0185172 A1 | 7/2010 | Fabro |
| 2010/0198056 A1 | 8/2010 | Fabro et al. |
| 2010/0198192 A1 | 8/2010 | Serina et al. |
| 2010/0198208 A1 | 8/2010 | Napp et al. |
| 2010/0217385 A1 | 8/2010 | Thompson et al. |
| 2010/0312333 A1 | 12/2010 | Navia et al. |
| 2011/0022164 A1 | 1/2011 | Quinn et al. |
| 2011/0046600 A1 | 2/2011 | Crank |
| 2011/0224785 A1 | 9/2011 | Hacohen |
| 2011/0288637 A1 | 11/2011 | De Marchena |
| 2011/0313515 A1 | 12/2011 | Quadri et al. |
| 2011/0319989 A1 | 12/2011 | Lane et al. |
| 2012/0022633 A1 | 1/2012 | Olson et al. |
| 2012/0053680 A1 | 3/2012 | Bolling et al. |
| 2012/0143316 A1 | 6/2012 | Seguin et al. |
| 2012/0197388 A1 | 8/2012 | Khairkhahan et al. |
| 2012/0203333 A1 | 8/2012 | McGuckin, Jr. et al. |
| 2012/0221101 A1 | 8/2012 | Moaddeb et al. |
| 2012/0277853 A1 | 11/2012 | Rothstein |
| 2013/0006352 A1 | 1/2013 | Yaron |
| 2013/0023985 A1 | 1/2013 | Khairkhahan et al. |
| 2013/0035758 A1 | 2/2013 | Seguin et al. |
| 2013/0079873 A1 | 3/2013 | Migliazza et al. |
| 2013/0123912 A1 | 5/2013 | Tung et al. |
| 2013/0172992 A1 | 7/2013 | Gross et al. |
| 2013/0253643 A1 | 9/2013 | Rolando et al. |
| 2013/0274873 A1 | 10/2013 | Delaloye et al. |
| 2013/0325110 A1 | 12/2013 | Khalil et al. |
| 2014/0005768 A1 | 1/2014 | Thomas et al. |
| 2014/0031928 A1 | 1/2014 | Murphy et al. |
| 2014/0081154 A1 | 5/2014 | Toth |
| 2014/0200649 A1 | 7/2014 | Essinger et al. |
| 2014/0228943 A1 | 8/2014 | Stigall et al. |
| 2014/0249621 A1 | 9/2014 | Eidenschink |
| 2014/0257467 A1 | 9/2014 | Lane et al. |
| 2014/0277382 A1 | 9/2014 | Dolan et al. |
| 2014/0277409 A1 | 9/2014 | Börtlein et al. |
| 2014/0324163 A1 | 10/2014 | Keränen et al. |
| 2014/0379074 A1 | 12/2014 | Spence et al. |
| 2015/0005764 A1 | 1/2015 | Hanson et al. |
| 2015/0018876 A1 | 1/2015 | Ewers et al. |
| 2015/0051709 A1 | 2/2015 | Vasquez et al. |
| 2015/0134055 A1 | 5/2015 | Spence et al. |
| 2015/0173897 A1 | 6/2015 | Raanani et al. |
| 2015/0250480 A1 | 9/2015 | Featherstone |
| 2015/0265403 A1 | 9/2015 | Keränen |
| 2015/0272737 A1 | 10/2015 | Dale et al. |
| 2015/0297346 A1 | 10/2015 | Duffy et al. |
| 2015/0305863 A1 | 10/2015 | Gray et al. |
| 2015/0328000 A1 | 11/2015 | Ratz et al. |
| 2015/0335290 A1 | 11/2015 | Hunter |
| 2015/0351735 A1 | 12/2015 | Keränen et al. |
| 2015/0351908 A1 | 12/2015 | Keränen et al. |
| 2015/0351911 A1 | 12/2015 | Keränen et al. |
| 2016/0089126 A1 | 3/2016 | Guo |
| 2016/0095705 A1 | 4/2016 | Keränen et al. |
| 2016/0113764 A1 | 4/2016 | Sheahan et al. |
| 2016/0143689 A1 | 5/2016 | Ditter |
| 2016/0143731 A1 | 5/2016 | Backus et al. |
| 2016/0166380 A1 | 6/2016 | Seguin et al. |
| 2016/0206853 A1* | 7/2016 | Bolduc ............ A61M 25/0136 |
| 2016/0228247 A1 | 8/2016 | Maimon et al. |
| 2016/0235526 A1 | 8/2016 | Lashinski et al. |
| 2016/0235529 A1 | 8/2016 | Ma et al. |
| 2016/0324637 A1 | 11/2016 | Hlavka et al. |
| 2016/0324639 A1 | 11/2016 | Nguyen et al. |
| 2016/0331523 A1 | 11/2016 | Chau et al. |
| 2016/0346080 A1 | 12/2016 | Righini et al. |
| 2017/0056163 A1 | 3/2017 | Tayeb et al. |
| 2017/0071732 A1 | 3/2017 | Conklin et al. |
| 2017/0079790 A1 | 3/2017 | Vidlund et al. |
| 2017/0112624 A1 | 4/2017 | Patel |
| 2017/0119524 A1 | 5/2017 | Salahieh et al. |
| 2017/0128203 A1 | 5/2017 | Zhang et al. |
| 2017/0156723 A1 | 6/2017 | Keating et al. |
| 2017/0165057 A9 | 6/2017 | Morriss et al. |
| 2017/0189177 A1 | 7/2017 | Schweich et al. |
| 2017/0216025 A1 | 8/2017 | Nitzan et al. |
| 2017/0245850 A1 | 8/2017 | Call et al. |
| 2017/0258585 A1 | 9/2017 | Marquez et al. |
| 2017/0273788 A1 | 9/2017 | O'Carroll et al. |
| 2017/0273789 A1 | 9/2017 | Yaron et al. |
| 2017/0281341 A1 | 10/2017 | Lim et al. |
| 2017/0311937 A1 | 11/2017 | Bambury et al. |
| 2017/0348099 A1 | 12/2017 | Mendelson et al. |
| 2018/0049873 A1 | 2/2018 | Manash et al. |
| 2018/0055628 A1 | 3/2018 | Patel et al. |
| 2018/0092763 A1 | 4/2018 | Dagan et al. |
| 2018/0110622 A1 | 4/2018 | Gregg et al. |
| 2018/0116790 A1 | 5/2018 | Ratz et al. |
| 2018/0133003 A1 | 5/2018 | Levi |
| 2018/0177592 A1 | 6/2018 | Benichou et al. |
| 2018/0177594 A1 | 6/2018 | Patel et al. |
| 2018/0206982 A1 | 7/2018 | Haivatov et al. |
| 2018/0206986 A1 | 7/2018 | Noe et al. |
| 2018/0206992 A1 | 7/2018 | Brown |

(56) References Cited

U.S. PATENT DOCUMENTS

| | | |
|---|---|---|
| 2018/0207395 A1 | 7/2018 | Bulman et al. |
| 2018/0214267 A1 | 8/2018 | Lally et al. |
| 2018/0214270 A1 | 8/2018 | Subramanian et al. |
| 2018/0221014 A1 | 8/2018 | Darabian |
| 2018/0228608 A1 | 8/2018 | Sheps et al. |
| 2018/0228610 A1 | 8/2018 | Lashinski et al. |
| 2018/0235443 A1 | 8/2018 | Smith et al. |
| 2018/0250126 A1 | 9/2018 | O'Connor et al. |
| 2018/0250132 A1 | 9/2018 | Ketai et al. |
| 2018/0263764 A1 | 9/2018 | Manash et al. |
| 2018/0289473 A1 | 10/2018 | Rajagopal et al. |
| 2018/0289474 A1 | 10/2018 | Rajagopal et al. |
| 2018/0289478 A1 | 10/2018 | Quill |
| 2018/0289480 A1 | 10/2018 | D'ambra et al. |
| 2018/0289485 A1 | 10/2018 | Rajagopal et al. |
| 2018/0296335 A1 | 10/2018 | Miyashiro |
| 2018/0296338 A1 | 10/2018 | Rabito et al. |
| 2018/0318079 A1* | 11/2018 | Patel .................... A61F 2/2436 |
| 2018/0325665 A1 | 11/2018 | Gurovich et al. |
| 2018/0333259 A1 | 11/2018 | Dibie |
| 2018/0344303 A1 | 12/2018 | Bambury et al. |
| 2018/0344454 A1 | 12/2018 | Mauch et al. |
| 2018/0344459 A1 | 12/2018 | Spence et al. |
| 2018/0360600 A1 | 12/2018 | Zhuang et al. |
| 2018/0368830 A1 | 12/2018 | O'Carroll et al. |
| 2019/0000615 A1 | 1/2019 | Tayeb et al. |
| 2019/0000625 A1 | 1/2019 | O'Carroll et al. |
| 2019/0008635 A1 | 1/2019 | Francis et al. |
| 2019/0008639 A1 | 1/2019 | Landon et al. |
| 2019/0008640 A1 | 1/2019 | Cooper et al. |
| 2019/0015205 A1 | 1/2019 | Rajagopal et al. |
| 2019/0021859 A1 | 1/2019 | O'Carrol et al. |
| 2019/0046315 A1 | 2/2019 | Gao et al. |
| 2019/0053894 A1 | 2/2019 | Levi et al. |
| 2019/0053895 A1 | 2/2019 | Levi |
| 2019/0053898 A1 | 2/2019 | Maimon et al. |
| 2019/0053899 A1 | 2/2019 | Levi |
| 2019/0053903 A1 | 2/2019 | Rohl et al. |
| 2019/0060068 A1 | 2/2019 | Cope et al. |
| 2019/0060069 A1 | 2/2019 | Maimon et al. |
| 2019/0060071 A1 | 2/2019 | Lane et al. |
| 2019/0076244 A1 | 3/2019 | Yohanan et al. |
| 2019/0076664 A1 | 3/2019 | Ollivier |
| 2019/0117392 A1 | 4/2019 | Quadri et al. |
| 2019/0133756 A1 | 5/2019 | Zhang et al. |
| 2019/0133757 A1 | 5/2019 | Zhang et al. |
| 2019/0142589 A1 | 5/2019 | Basude |
| 2019/0159770 A1 | 5/2019 | Rohl et al. |
| 2019/0160292 A1 | 5/2019 | Peichel et al. |
| 2019/0167425 A1 | 6/2019 | Reich et al. |
| 2019/0183649 A1 | 6/2019 | Allen et al. |
| 2019/0192296 A1 | 6/2019 | Schwartz et al. |
| 2019/0201191 A1 | 7/2019 | McLean et al. |
| 2019/0209311 A1 | 7/2019 | Zhang et al. |
| 2019/0209312 A1 | 7/2019 | Zhang et al. |
| 2019/0209313 A1 | 7/2019 | Zhang et al. |
| 2019/0209314 A1 | 7/2019 | Zhang et al. |
| 2019/0209315 A1 | 7/2019 | Zhang et al. |
| 2019/0209316 A1 | 7/2019 | Zhang et al. |
| 2019/0209317 A1 | 7/2019 | Zhang et al. |
| 2019/0209318 A1 | 7/2019 | Zhang et al. |
| 2019/0209320 A1 | 7/2019 | Draster et al. |
| 2019/0231520 A1 | 8/2019 | Desrosiers et al. |
| 2019/0240023 A1 | 8/2019 | Spence et al. |
| 2019/0246916 A1 | 8/2019 | Kuraguntla et al. |
| 2019/0254816 A1 | 8/2019 | Anderson et al. |
| 2019/0261995 A1 | 8/2019 | Goldfarb et al. |
| 2019/0261996 A1 | 8/2019 | Goldfarb et al. |
| 2019/0261997 A1 | 8/2019 | Goldfarb et al. |
| 2019/0262129 A1 | 8/2019 | Cooper et al. |
| 2019/0282237 A1 | 9/2019 | Goldfarb et al. |
| 2019/0328518 A1 | 10/2019 | Neumann |
| 2019/0336282 A1 | 11/2019 | Christianson et al. |
| 2019/0343625 A1 | 11/2019 | Gharib et al. |
| 2019/0365530 A1 | 12/2019 | Hoang et al. |
| 2019/0374337 A1 | 12/2019 | Zamani et al. |
| 2019/0374342 A1 | 12/2019 | Gregg et al. |
| 2020/0000579 A1 | 1/2020 | Manash et al. |
| 2020/0000586 A1 | 1/2020 | Tian et al. |
| 2020/0008936 A1 | 1/2020 | Cheema et al. |
| 2020/0022811 A1 | 1/2020 | Griswold et al. |
| 2020/0054453 A1 | 2/2020 | Zerkowski et al. |
| 2020/0060813 A1 | 2/2020 | Nguyen et al. |
| 2020/0060820 A1 | 2/2020 | Ben-Zvi et al. |
| 2020/0060852 A1 | 2/2020 | Argento et al. |
| 2020/0078000 A1 | 3/2020 | Rajagopal et al. |
| 2020/0093601 A1 | 3/2020 | Neustadter |
| 2020/0107932 A1* | 4/2020 | Rabito ............... A61B 17/0401 |
| 2020/0107933 A1 | 4/2020 | Oba |
| 2020/0113586 A1 | 4/2020 | Karasic et al. |
| 2020/0113685 A1 | 4/2020 | Miller et al. |
| 2020/0113696 A1 | 4/2020 | Ekvall et al. |
| 2020/0138575 A1 | 5/2020 | Tuval |
| 2020/0139082 A1* | 5/2020 | Matlock ................. B29C 48/34 |
| 2020/0178977 A1 | 6/2020 | Coleman et al. |
| 2020/0188107 A1 | 6/2020 | Gloss et al. |
| 2020/0205800 A1 | 7/2020 | Gilmore et al. |
| 2020/0205969 A1 | 7/2020 | Hacohen |
| 2020/0205974 A1 | 7/2020 | Zerkowski et al. |
| 2020/0205975 A1 | 7/2020 | Khairkhahan |
| 2020/0205979 A1 | 7/2020 | O'Carroll et al. |
| 2020/0214708 A1 | 7/2020 | Sharma |
| 2020/0229806 A1 | 7/2020 | Goldfarb et al. |
| 2020/0229918 A1 | 7/2020 | Pham et al. |
| 2020/0261220 A1 | 8/2020 | Argento et al. |
| 2020/0275921 A1 | 9/2020 | Gilmore et al. |
| 2020/0276017 A1 | 9/2020 | Subramanian et al. |
| 2020/0297489 A1 | 9/2020 | Bishop et al. |
| 2020/0352705 A1 | 11/2020 | Heneghan et al. |
| 2020/0352706 A1 | 11/2020 | Campbell |
| 2020/0360139 A1 | 11/2020 | Hammer et al. |
| 2021/0022854 A1 | 1/2021 | Zhao et al. |
| 2021/0022860 A1 | 1/2021 | Lally et al. |
| 2021/0030536 A1 | 2/2021 | Kaleta |
| 2021/0121289 A1 | 4/2021 | Bruchman et al. |
| 2021/0128297 A1 | 5/2021 | Braido et al. |
| 2021/0145573 A1 | 5/2021 | Dasi et al. |
| 2021/0161688 A1 | 6/2021 | Shahriari |
| 2021/0177583 A1 | 6/2021 | Colavito et al. |
| 2021/0177584 A1 | 6/2021 | Levi et al. |
| 2021/0177587 A1 | 6/2021 | Braido |
| 2021/0186689 A1 | 6/2021 | Eidenschink et al. |
| 2021/0228343 A1 | 7/2021 | Scheinblum et al. |
| 2021/0378823 A1 | 12/2021 | Argento et al. |
| 2021/0401572 A1 | 12/2021 | Nasar et al. |
| 2022/0054261 A1 | 2/2022 | Argento et al. |
| 2022/0175522 A1 | 6/2022 | Salahieh et al. |
| 2022/0257373 A1 | 8/2022 | Yang et al. |
| 2022/0401214 A1 | 12/2022 | Saul |
| 2023/0044256 A1 | 2/2023 | Salahleh |
| 2023/0105492 A1 | 4/2023 | Argento et al. |
| 2023/0118748 A1 | 4/2023 | Argento |
| 2023/0165679 A1 | 6/2023 | Boyd et al. |

FOREIGN PATENT DOCUMENTS

| | | |
|---|---|---|
| AU | 2020227034 A1 | 9/2020 |
| BR | PI0820603 B1 | 6/2020 |
| CA | 2979817 A1 | 9/2016 |
| CA | 2954826 C | 10/2019 |
| CN | 103764216 A | 4/2014 |
| CN | 103974670 A | 8/2014 |
| CN | 105358098 A | 2/2016 |
| CN | 111110401 A | 5/2020 |
| CN | 111110403 A | 5/2020 |
| CN | 108601655 B | 6/2020 |
| CN | 111265335 A | 6/2020 |
| CN | 111278389 A | 6/2020 |
| CN | 111329541 A | 6/2020 |
| DE | 19857887 B4 | 5/2005 |
| DE | 102014102650 A1 | 9/2015 |
| EP | 1432369 B1 | 2/2008 |
| EP | 2374415 A1 | 10/2011 |
| EP | 2907479 A1 | 8/2015 |

(56) References Cited

FOREIGN PATENT DOCUMENTS

| | | |
|---|---|---|
| EP | 3037064 A1 | 6/2016 |
| EP | 3342355 A1 | 7/2018 |
| EP | 3395296 A1 | 10/2018 |
| EP | 3406225 A1 | 11/2018 |
| EP | 3417831 A1 | 12/2018 |
| EP | 3476366 A1 | 5/2019 |
| EP | 3482718 A1 | 5/2019 |
| EP | 2637607 B1 | 10/2019 |
| EP | 3554424 A1 | 10/2019 |
| EP | 3244809 B1 | 2/2020 |
| EP | 3639792 A1 | 4/2020 |
| EP | 3417831 B1 | 5/2020 |
| EP | 3649963 A2 | 5/2020 |
| EP | 2072027 B1 | 6/2020 |
| EP | 3441045 B1 | 7/2020 |
| EP | 3672528 A1 | 7/2020 |
| EP | 3554423 B1 | 8/2020 |
| EP | 3107498 B1 | 9/2020 |
| EP | 3570782 B1 | 9/2020 |
| EP | 3700467 A1 | 9/2020 |
| EP | 3705090 A1 | 9/2020 |
| EP | 3782585 A1 | 2/2021 |
| JP | H08131551 A | 5/1996 |
| JP | 2004154177 A | 6/2004 |
| JP | 2008018139 A | 1/2008 |
| JP | 2011506017 A | 3/2011 |
| JP | 2012531270 A | 12/2012 |
| JP | 2020515375 A | 5/2020 |
| JP | 2020517379 A | 6/2020 |
| JP | 2020520729 A | 7/2020 |
| JP | 6735294 B2 | 8/2020 |
| KR | 2020032237 A | 3/2020 |
| KR | 2020033349 A | 3/2020 |
| KR | 2020033350 A | 3/2020 |
| TW | 202027694 A | 8/2020 |
| WO | WO2007/007873 A1 | 1/2007 |
| WO | WO2007/081820 A1 | 7/2007 |
| WO | WO2010/141847 A1 | 12/2010 |
| WO | WO2011/025945 A1 | 3/2011 |
| WO | WO2012/087842 A1 | 6/2012 |
| WO | WO2012/145545 A1 | 10/2012 |
| WO | WO2013/190910 A1 | 12/2013 |
| WO | WO2015/127264 A1 | 8/2015 |
| WO | WO2015/173609 A1 | 11/2015 |
| WO | WO2015/195823 A1 | 12/2015 |
| WO | WO2016/052145 A1 | 4/2016 |
| WO | WO2016/117169 A1 | 7/2016 |
| WO | WO2016/183485 A1 | 11/2016 |
| WO | WO2017/121193 A1 | 7/2017 |
| WO | WO2017/151566 A1 | 9/2017 |
| WO | WO2017/214098 A1 | 12/2017 |
| WO | WO2018/025260 A1 | 2/2018 |
| WO | WO2018/039561 A1 | 3/2018 |
| WO | WO2018/039589 A1 | 3/2018 |
| WO | WO2018/112429 A1 | 6/2018 |
| WO | WO2018/119304 A1 | 6/2018 |
| WO | WO2018/178966 A1 | 10/2018 |
| WO | WO2018/178967 A1 | 10/2018 |
| WO | WO2018/187390 A1 | 10/2018 |
| WO | WO2018/192197 A1 | 10/2018 |
| WO | WO2019/010370 A1 | 1/2019 |
| WO | WO2019/036592 A1 | 2/2019 |
| WO | WO2019/062366 A1 | 4/2019 |
| WO | WO2019/081777 A1 | 5/2019 |
| WO | WO2019/086958 A1 | 5/2019 |
| WO | WO2019/102484 A1 | 5/2019 |
| WO | WO2019/116369 A1 | 6/2019 |
| WO | WO2019/118371 A1 | 6/2019 |
| WO | WO2019/135011 A1 | 7/2019 |
| WO | WO2019/135028 A1 | 7/2019 |
| WO | WO2019/144036 A1 | 7/2019 |
| WO | WO2019/147504 A1 | 8/2019 |
| WO | WO2019/147846 A2 | 8/2019 |
| WO | WO2019/154124 A1 | 8/2019 |
| WO | WO2019/164516 A1 | 8/2019 |
| WO | WO2019/195860 A2 | 10/2019 |
| WO | WO2019/209927 A1 | 10/2019 |
| WO | WO2019/222694 A1 | 11/2019 |
| WO | WO2019/241777 A1 | 12/2019 |
| WO | WO2020/051147 A1 | 3/2020 |
| WO | WO2020/051591 A1 | 3/2020 |
| WO | WO2020/072199 A1 | 4/2020 |
| WO | WO2020/072201 A1 | 4/2020 |
| WO | WO2020/073050 A1 | 4/2020 |
| WO | WO2020/123719 A1 | 6/2020 |
| WO | WO2020/132590 A1 | 6/2020 |
| WO | WO2020/157018 A1 | 8/2020 |
| WO | WO2020/163112 A1 | 8/2020 |
| WO | WO2020/236830 A1 | 11/2020 |
| WO | WO2020/247907 A1 | 12/2020 |
| WO | WO2021/021482 A1 | 2/2021 |
| WO | WO2021/028867 A1 | 2/2021 |
| WO | WO2021/034497 A1 | 2/2021 |
| WO | WO2021/086850 A1 | 5/2021 |
| WO | WO2021/091754 A1 | 5/2021 |
| WO | WO2021/113143 A1 | 6/2021 |
| WO | WO2021/178560 A1 | 9/2021 |
| WO | WO2021/183610 A1 | 9/2021 |
| WO | WO2021/257278 A1 | 12/2021 |
| WO | WO2021/257722 A1 | 12/2021 |
| WO | WO2022/010974 A1 | 1/2022 |
| WO | WO2022/046678 A1 | 3/2022 |
| WO | WO2022/047095 A1 | 3/2022 |
| WO | WO2022/047160 A1 | 3/2022 |
| WO | WO2022/047274 A1 | 3/2022 |
| WO | WO2022/047393 A8 | 3/2022 |
| WO | WO2022/047395 A1 | 3/2022 |

OTHER PUBLICATIONS

Argento et al.; U.S. Appl. No. 17/931,408 entitled "Prosthetic cardiac valve devices, systems, and methods,", filed Sep. 12, 2022.
Argento et al.; U.S. Appl. No. 18/002,219 entitled "Minimal frame prosthetic cardiac valve delivery devices, systems, and methods,", filed Dec. 16, 2022.
Backus et al.; U.S. Appl. No. 18/004,609 entitled "Valve delivery system," filed Jan. 6, 2023.
Mulcahy et al.; U.S. Appl. No. 18/043,480 entitled "Prosthetic cardiac valve delivery devices, systems, and methods,", filed Feb. 28, 2023.
Adamek-Bowers et al.; U.S. Appl. No. 18/043,499 entitled "Interface for prosthetic cardiac valve and delivery systems,", filed Feb. 28, 2023.
Salahieh et al.; U.S. Appl. No. 18/043,519 entitled "Flared prosthetic cardiac valve delivery devices and systems,", filed Feb. 28, 2023.
Scott et al.; U.S. Appl. No. 18/043,526 entitled "Access sheath for prosthetic cardiac valve delivery systems,", filed Feb. 28, 2023.
Yang et al.; U.S. Appl. No. 18/043,542 entitled "Anchor for prosthetic cardiac valve devices,", filed Feb. 28, 2023.
Argento et al.; U.S. Appl. No. 18/246,307 entitled "Systems, methods, and devices for expandable sensors,", filed Mar. 22, 2023.
Argento et al.; U.S. Appl. No. 18/246,311 entitled "Prosthetic cardiac valve sensor devices, systems, and methods with imaging," filed Mar. 22, 2023.
Westaby et al.; Adult human valve dimensions and their surgical significance; The American Journal of Cardiology; 53(4); pp. 552-556; Feb. 1984.
Argento et al.; U.S. Appl. No. 18/185,330 entitled "Prosthetic cardiac valve devices, systems, and methods,", filed Mar. 16, 2023.
Adamek-Bowers et al.; U.S. Appl. No. 18/255,763 entitled "Mitral valve implants,", filed Jun. 2, 2023.
Argento et al.; U.S. Appl. No. 18/494,520 entitled "Prosthetic cardiac valve devices, systems, and methods,", filed Oct. 25, 2023.

* cited by examiner

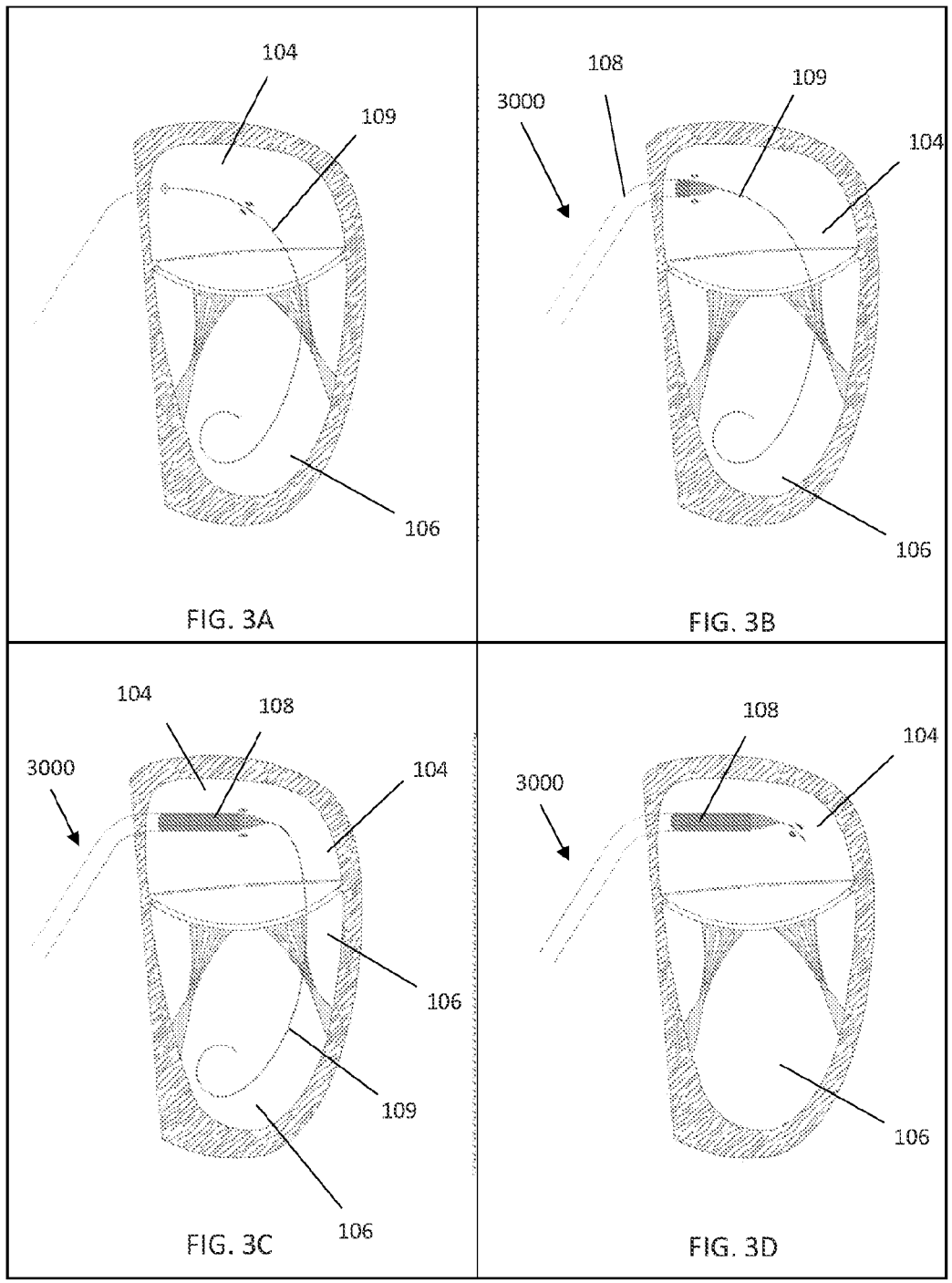

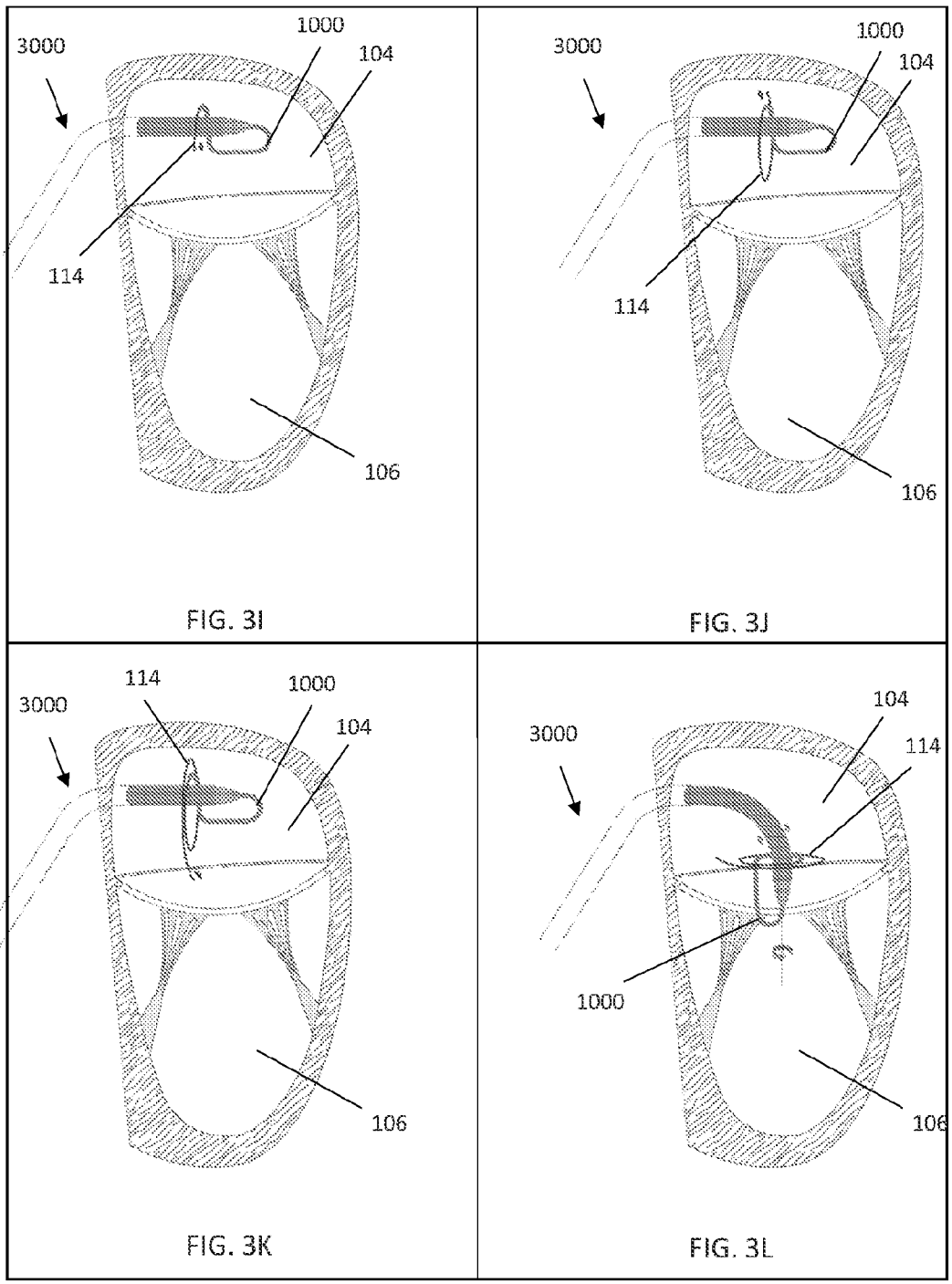

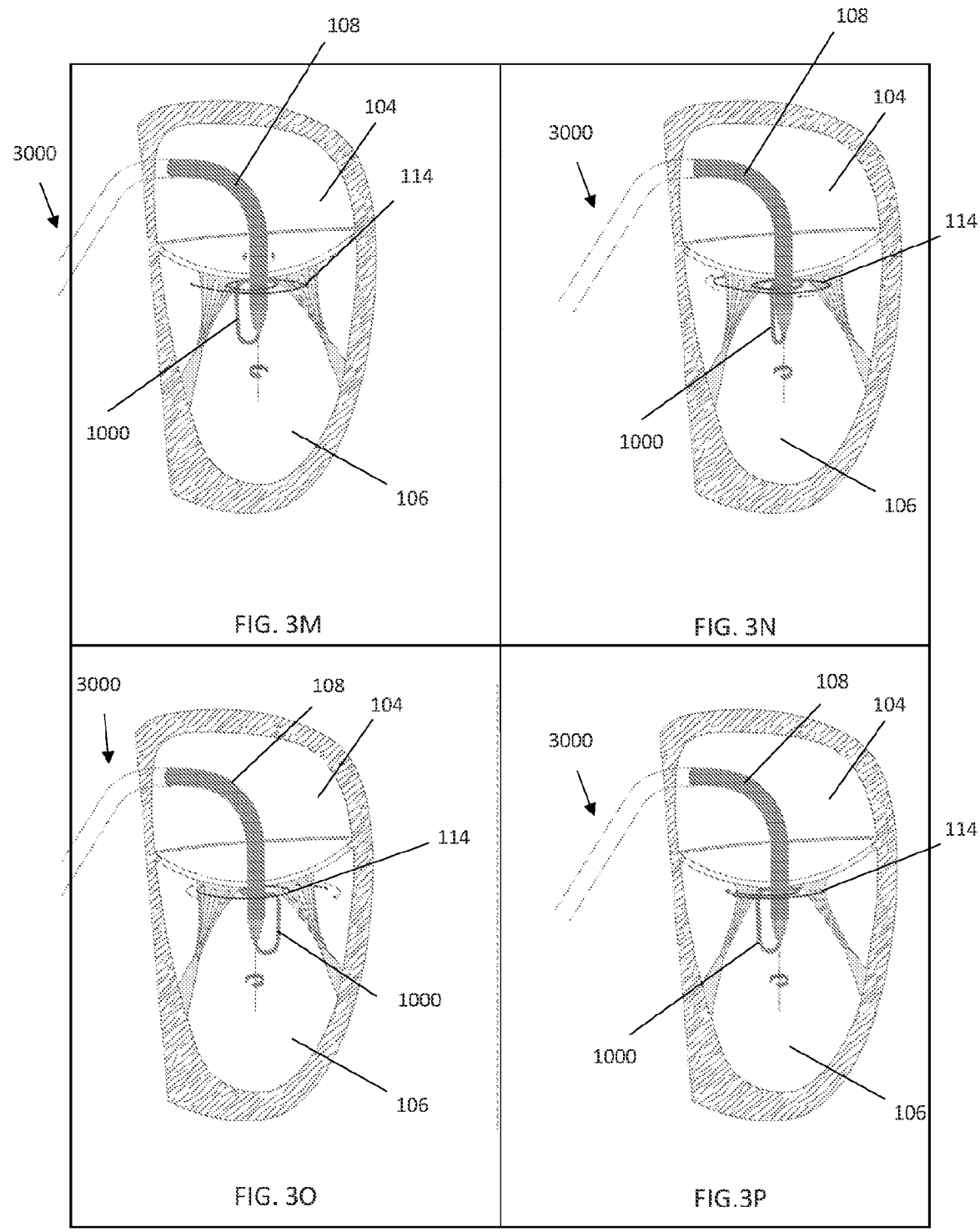

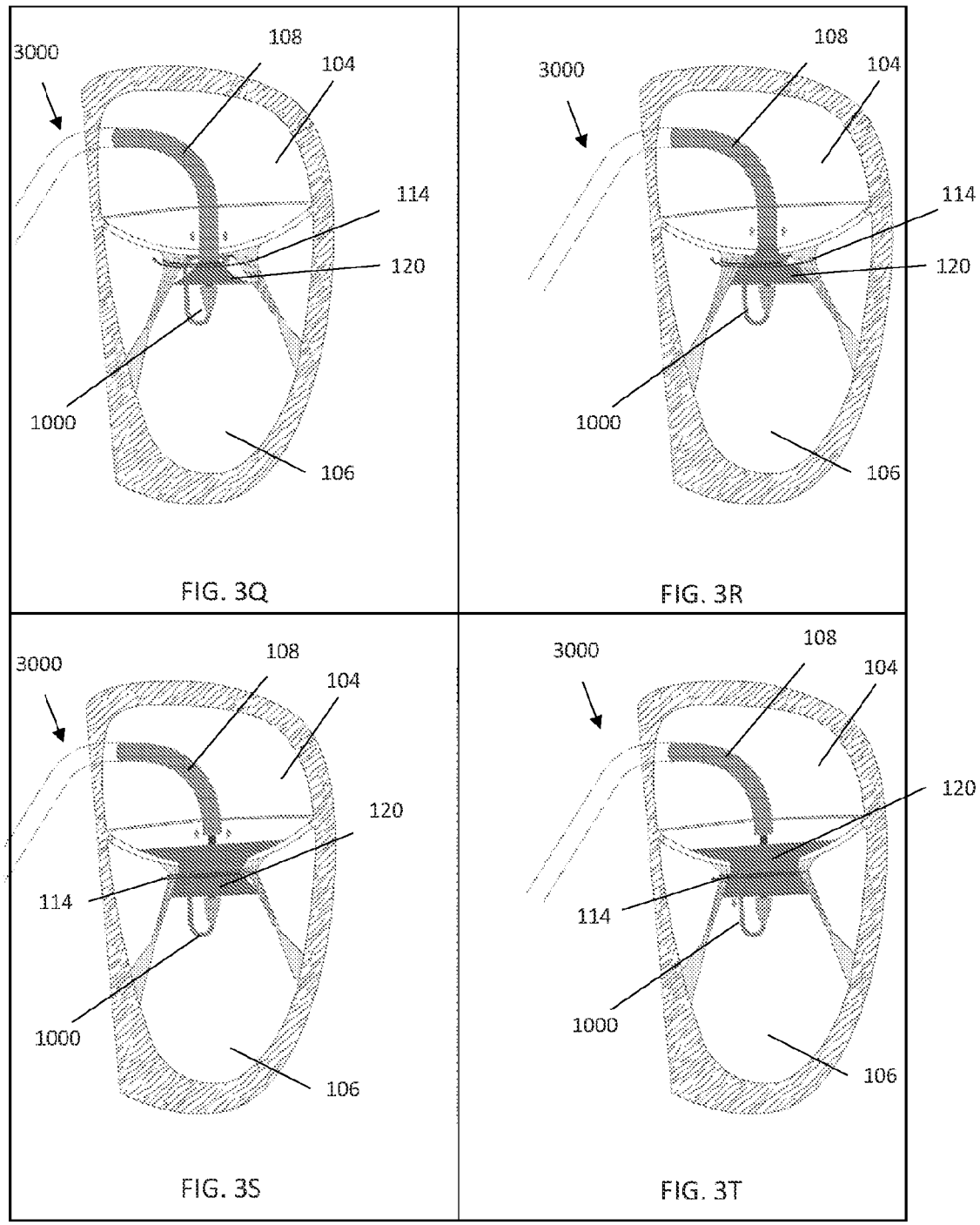

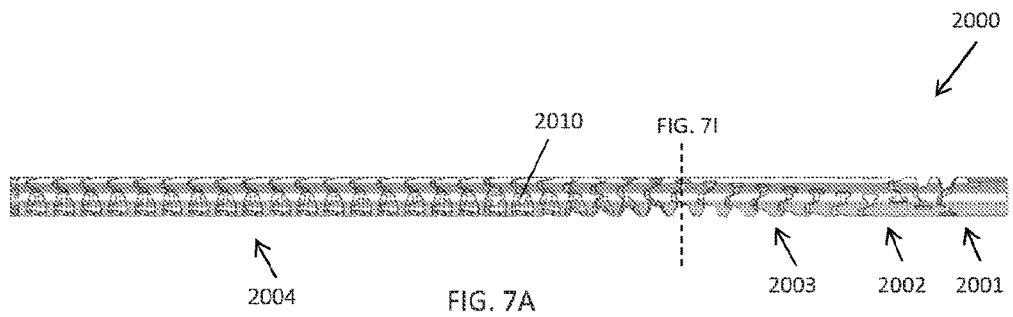
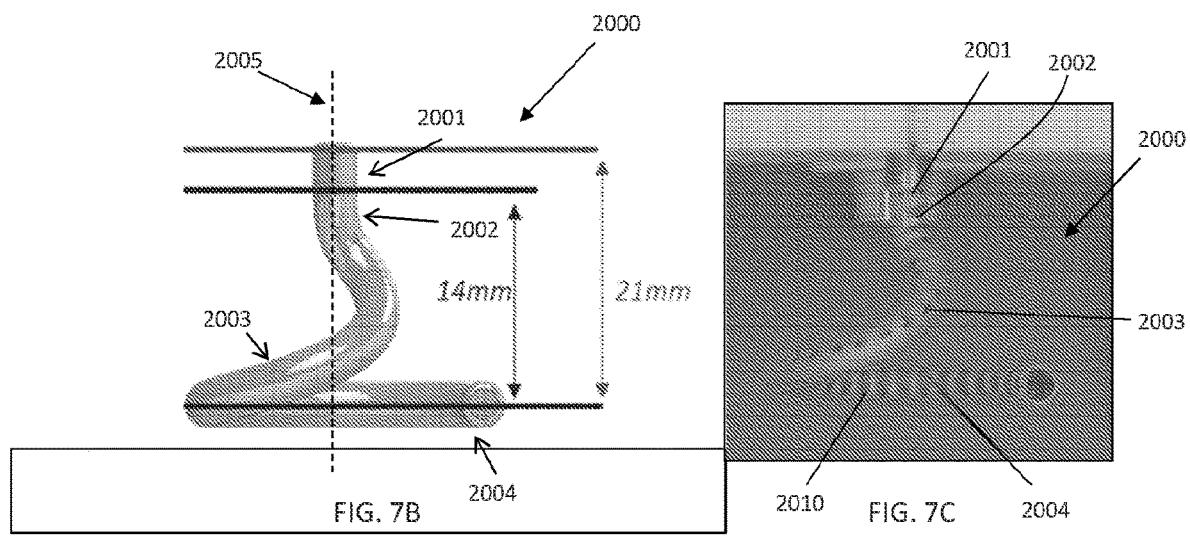
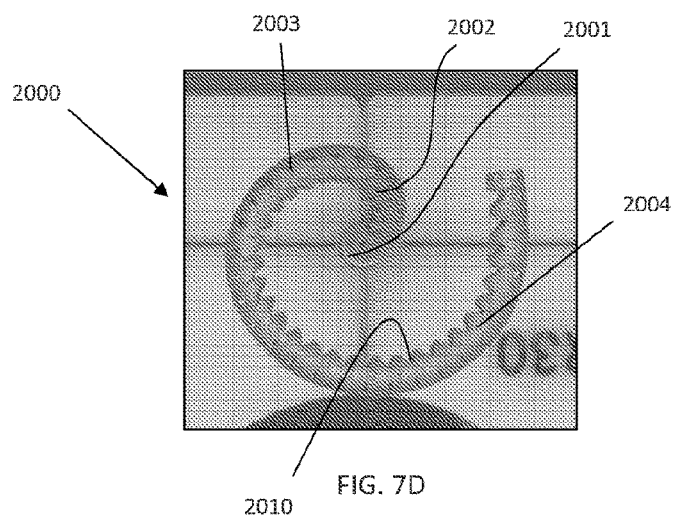

PROSTHETIC VALVE DELIVERY SYSTEM

CROSS REFERENCE TO RELATED APPLICATIONS

This application claims priority to U.S. Provisional Patent Application No. 63/072,788, filed on Aug. 31, 2020, titled "VALVE DELIVERY SYSTEM," the entirety of which is incorporated by reference herein.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

Blood flow between heart chambers is regulated by native valves—the mitral valve, the aortic valve, the pulmonary valve, and the tricuspid valve. Each of these valves are passive one-way valves which open and close in response to differential pressures. Patients with valvular disease have abnormal anatomy and/or function of at least one valve. For example, a valve may suffer from insufficiency, also referred to as regurgitation, when the valve does not fully close and allows blood to flow retrograde. Valve stenosis can cause a valve to fail to open properly. Other diseases may also lead to dysfunction of the valves. While medications may be used to treat the disease, in many cases the defective valve may need to be repaired or replaced at some point during the patient's lifetime. Existing valves and surgical repair and/or replacement procedures may have relatively high risks, limited lifespans, and/or be highly invasive. Some less-invasive transcatheter options are available, however these generally are limited to aortic valve procedures, are limited in patient-to-patient flexibility, and often take longer than is desirable to implant. It would therefore be desirable to provide a less invasive procedure for repair and replacement of heart valves, including the mitral valve, quicker surgical methods, and/or prosthetic valves that can accommodate a variety of individual patients.

Additionally, existing valve repair/replacement procedures are often complicated and time-consuming. Presently-available procedures often require the placement of more than one component—for example, a prosthetic valve and a mechanism to anchor it to the native anatomy. Such procedures generally utilize multiple delivery catheters to carry the various components and delivery of each component separately to the valve, which can be time-consuming (particularly if components are delivered sequentially), complicated, and/or dangerous. For example, some devices provide rotational anchoring elements to capture the native anatomy such as the chordae tendineae in order to reduce delivery time. However, such anchoring elements, often by design, capture and pull the chordae along during their rotation, which can torque or otherwise stress and damage the chordae during deployment of the anchor elements, resulting in the need for additional medical interventions for the patient. Moreover, such anchoring elements may require extrusion from a low-profile (e.g., elongated) delivery configuration to an expanded configuration at or near the native valve. In at least some instances, extrusion of the anchoring elements can be complicated and may not reliably deploy into the correct expanded configuration relative to the delivery device and/or the native anatomy. Incorrect deployment may result in additional time to retract and re-deploy the anchoring element, more complicated anchoring procedures, and/or damage to the native tissue. It would therefore be desirable to provide quicker, less-complicated, less dangerous, and more reliably deployable valve assemblies for valvular replacement and repair.

SUMMARY OF THE DISCLOSURE

In general, in one embodiment, a delivery system for delivering a spiral anchor to a diseased native valve of a heart includes an anchor control catheter and an anchor guide extending from the anchor control catheter. The anchor guide includes a flexible configuration and a rigid configuration. The anchor guide in the rigid configuration includes a proximal section, a middle section, and a distal section. The proximal section includes a straight central axis and extends from the anchor control catheter, the middle section spirals axially and radially outwards from the central axis, and the distal section curves concentrically about the central axis in a plane that is perpendicular to the central axis.

This and other embodiments can include one or more of the following features. The anchor guide can include a plurality of cuts configured to define a shape of the guide in the rigid configuration. The plurality of cuts can include window cuts, interlocking spiral cuts, or toothed wedge cuts. The delivery system can further include one or more actuation elements configured to actuate the guide from the flexible configuration to the rigid configuration. The one or more actuation elements can include a nested concentric shaft mechanism or one or more pullwires or cables. The anchor guide can include an intermediate shape-set configuration configured to bias or urge the anchor guide towards the rigid configuration. The anchor guide can include a shape memory material. The anchor guide can include a central channel configured to hold an anchor therein. The anchor guide can be configured to deflect the anchor positioned within the central channel when the anchor guide is transitioned from the flexible configuration to the rigid configuration. The anchor guide can be configured to position the anchor concentrically relative to a central axis of the anchor control catheter. The anchor guide in the flexible configuration can be configured to be positioned within a delivery sheath.

In general, in one embodiment, a method of delivering a valve prosthesis to a diseased native valve of a heart includes positioning a delivery catheter in a first chamber of the heart, actuating an anchor guide of the delivery catheter from a flexible configuration to a rigid configuration, releasing an anchor from within the anchor guide, moving the delivery catheter from the first chamber to a second chamber of the heart such that the anchor guide in the rigid configuration is within the second chamber and the anchor is positioned concentrically relative to central axis of the delivery device, and rotating the anchor guide in the rigid configuration about the central axis so as to rotate the anchor and encircle chordae of the native heart with the anchor.

This and other embodiments can include one or more of the following features. The method can further include delivering a valve frame within the anchor after the step of rotating the anchor guide. Delivering the valve frame can include delivering the valve frame from a separate valve delivery catheter. A distal section of the anchor guide can curve concentrically relative to the central axis when the anchor guide is in the rigid configuration. Releasing the anchor can include releasing the anchor concentrically relative to the central axis. The method can further include adjusting a placement of the anchor with the anchor guide after the step of rotating the anchor guide. Adjusting the placement can include placing torque on the anchor with the anchor guide. Adjusting the placement can include moving the anchor proximally towards a valve annulus with the anchor guide. The diseased native valve can be a mitral valve, the first chamber can be an atrium, and the second chamber can be a ventricle. The method can further include counter-rotating the anchor guide during the step of moving the delivery catheter from the first chamber to the second chamber. An entirety of the anchor can be positioned within the second chamber and not the first chamber after the step of moving the delivery catheter from the first chamber to the second chamber. Releasing the anchor from within the anchor guide can include releasing the anchor while the anchor guide is in the rigid configuration. Releasing the anchor from within the anchor guide can include releasing the anchor while the anchor guide is an intermediate shape set configuration, and the releasing step can occur before the step of actuating an anchor guide of the delivery catheter from a flexible configuration to a rigid configuration.

In general, in one embodiment, a delivery system for delivering a spiral anchor to a diseased native valve of a heart includes an anchor control catheter and an anchor guide extending from the anchor control catheter. The anchor guide has a flexible configuration and a rigid configuration. The anchor guide in the rigid configuration includes a proximal section, a middle section, and a distal section. The proximal section extends from the anchor control catheter, the middle section includes an inversion, and the distal section is concentrically wrapped about the proximal section.

This and other embodiments can include one or more of the following features. The anchor guide can include a plurality of cuts configured to define a shape of the guide in the rigid configuration. The plurality of cuts can include window cuts, interlocking spiral cuts, or toothed wedge cuts. The delivery system can further include one or more actuation elements configured to actuate the guide from the flexible configuration to the rigid configuration. The one or more actuation elements can include a nested concentric shaft mechanism or one or more pullwires or cables. The anchor guide can include an intermediate shape-set configuration configured to bias or urge the anchor guide towards the rigid configuration. The anchor guide can include a shape memory material. The anchor guide can include a central channel configured to hold an anchor therein. The anchor guide can be configured to deflect the anchor positioned with the central channel when the anchor guide transitions from the flexible configuration to the rigid configuration. The anchor guide can be configured to position the anchor concentrically relative to a central axis of the anchor delivery catheter. The anchor guide in the flexible configuration can be configured to be positioned within a delivery sheath. The delivery system can further include an outer sheath positioned over the anchor control catheter and configured to house a prosthetic valve therein. The outer sheath can be configured to be retracted proximally to allow the prosthetic valve to self-expand around the anchor guide.

In general, in one embodiment, a method of delivering a valve prosthesis to a diseased native valve of a heart includes positioning a delivery catheter in a first chamber of the heart, actuating an anchor guide of the delivery catheter from a flexible configuration to a rigid configuration, releasing an anchor from within the anchor guide while the anchor guide is in the rigid configuration, moving the delivery catheter from the first chamber to a second chamber of the heart such that the anchor guide is inverted within the second chamber and the anchor is positioned concentrically around the delivery catheter, and rotating the anchor guide so as to rotate the anchor and encircle chordae of the native heart with the anchor.

This and other embodiments can include one or more of the following features. The method can further include delivering a valve frame within the anchor after the step of rotating the anchor guide. Delivering the valve frame can include delivering the valve frame from within the delivery catheter. Delivering the valve frame can include delivering the valve frame from a separate valve delivery catheter. A distal section of the anchor guide can wrap concentrically about a proximal section of the anchor guide when the anchor guide is in the rigid configuration. Releasing the anchor can include releasing the anchor concentrically relative to the delivery catheter. The method can further include adjusting a placement of the anchor with the anchor guide after the step of rotating the anchor guide. Adjusting the placement can include placing torque on the anchor with the anchor guide. Adjusting the placement can include moving the anchor proximally towards a valve annulus with the anchor guide. The diseased native valve can be a mitral valve, the first chamber is an atrium, and the second chamber is a ventricle. The method can further include counter-rotating the anchor guide during the step of moving the delivery catheter from the first chamber to the second chamber. An entirety of the anchor can be positioned within the second chamber and not the first chamber after the step of moving the delivery catheter from the first chamber to the second chamber.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 7A-7I show another embodiment of an anchor guide.

DETAILED DESCRIPTION

Described herein are devices and methods for use in delivering a valve prosthesis, including an anchor and/or frame, for example during a mitral valve replacement.

Figure 1A:
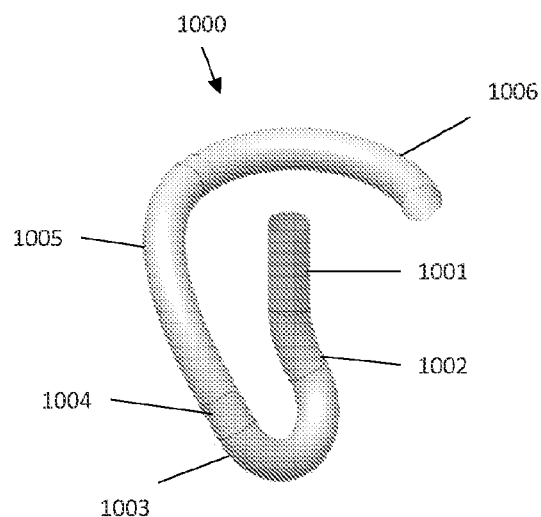
FIGS. 1A-1C illustrates a delivery system including an inverted anchor guide.
Figure 1B:
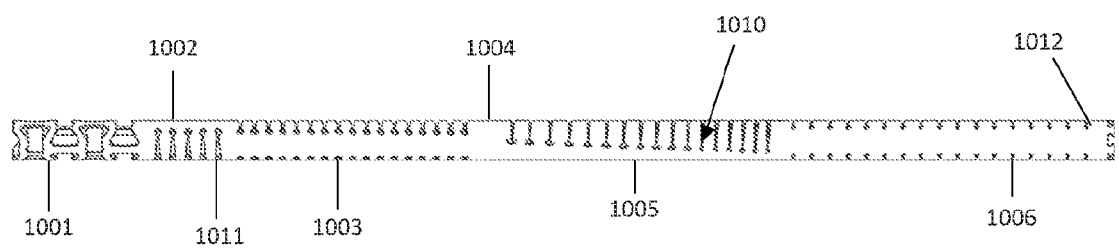
Figure 1C:
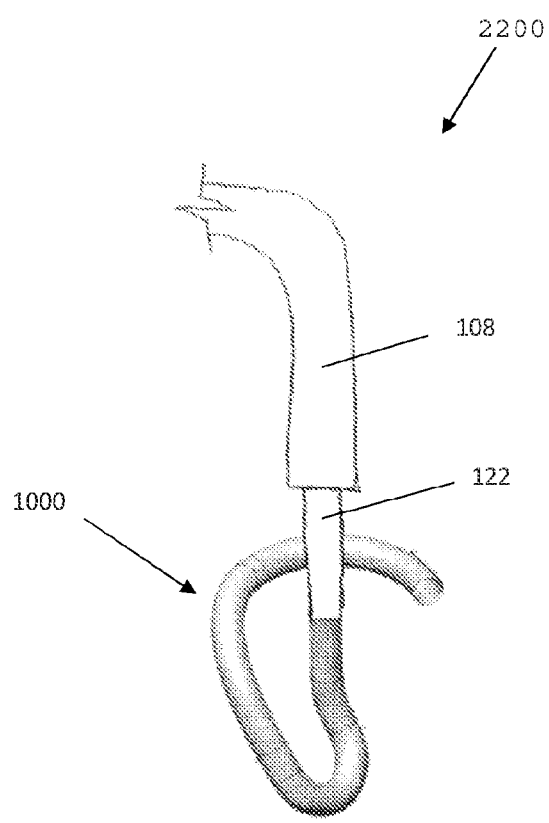
Figure 2A:
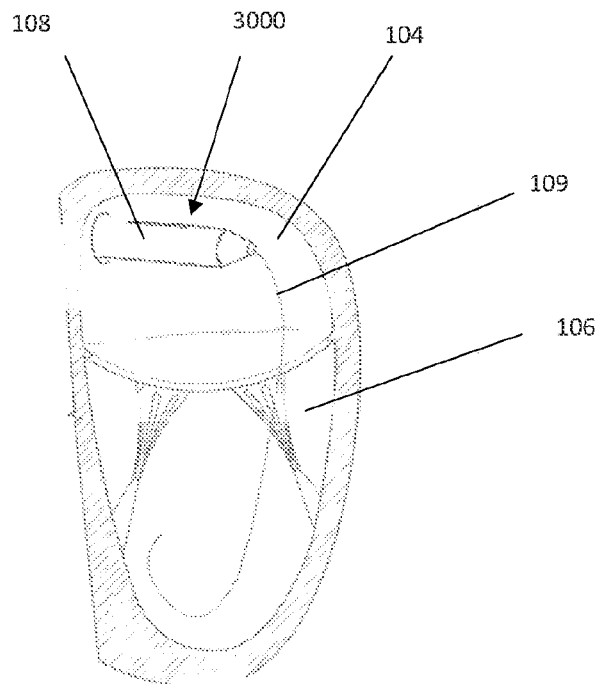
FIGS. 2A-2H show an embodiment of a method of delivering an anchor and a valve prosthesis near a native valve annulus using an inverted guide and a single valve delivery catheter.
Figure 2B:
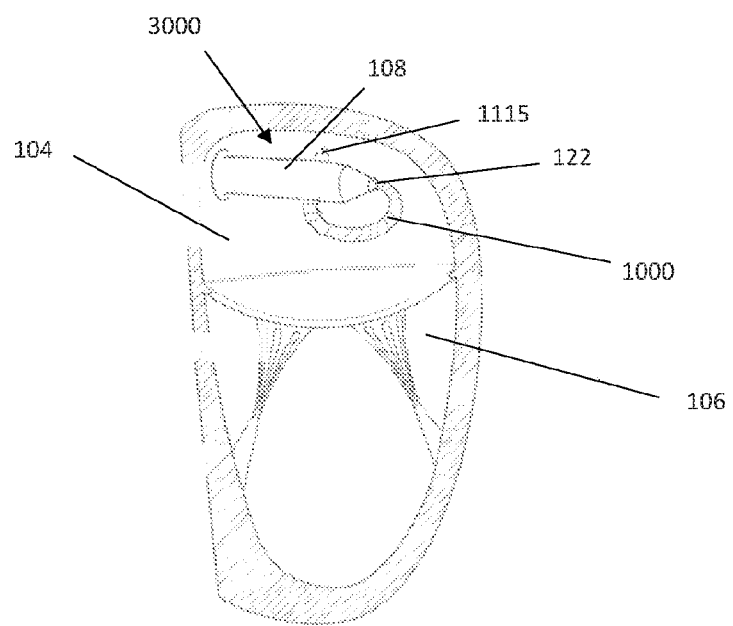
Figure 2C:
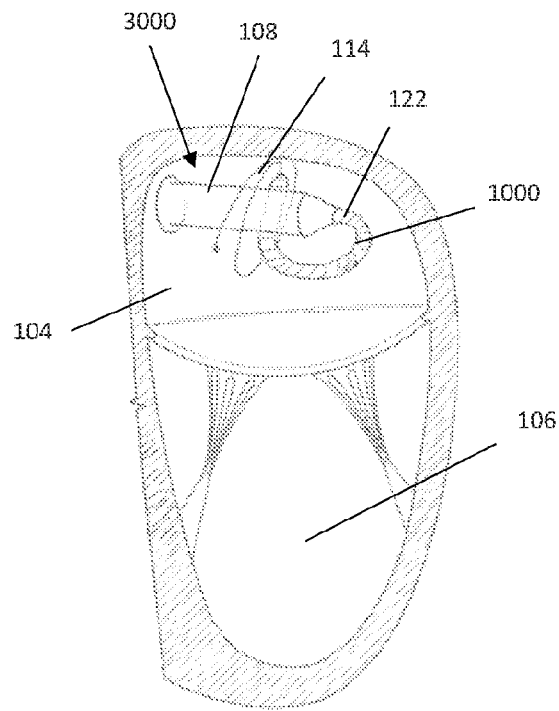
Figure 2D:
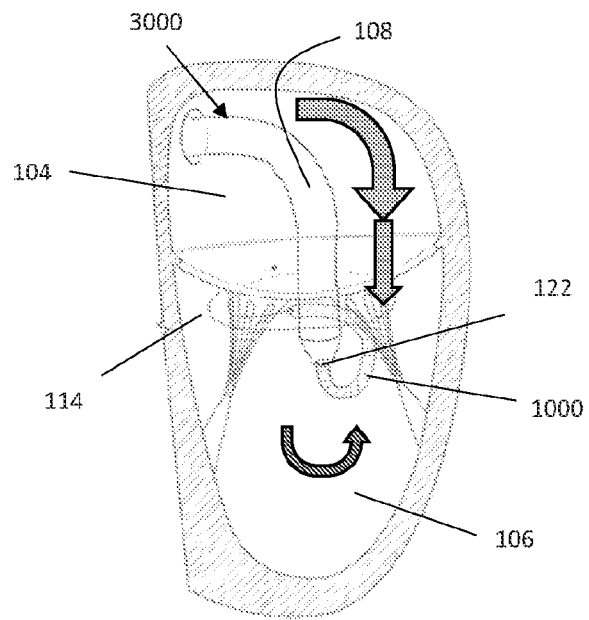
Figure 2E:
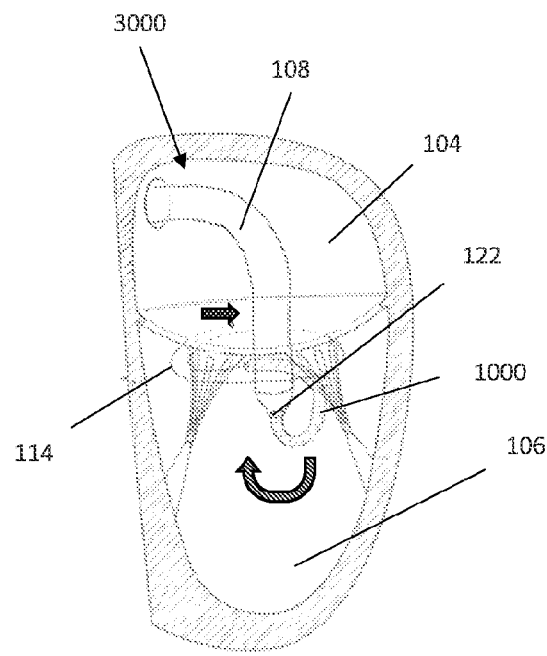
Figure 2F:
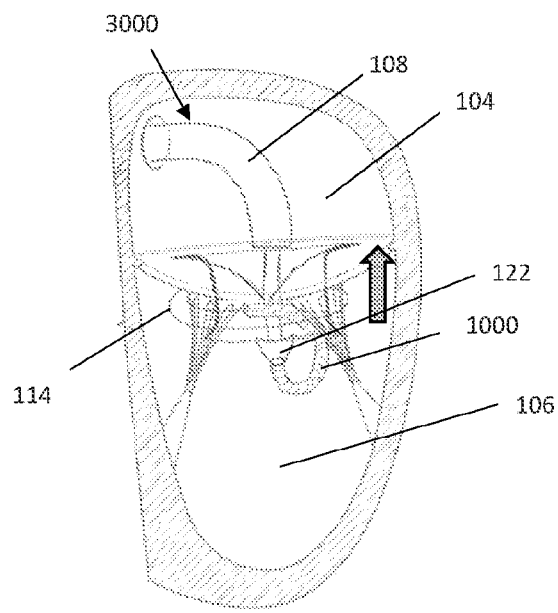
Figure 2G:
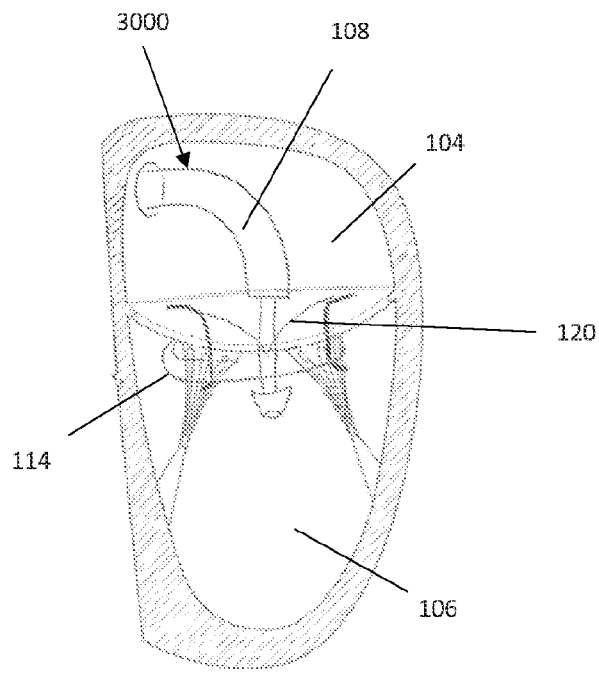
Figure 2H:
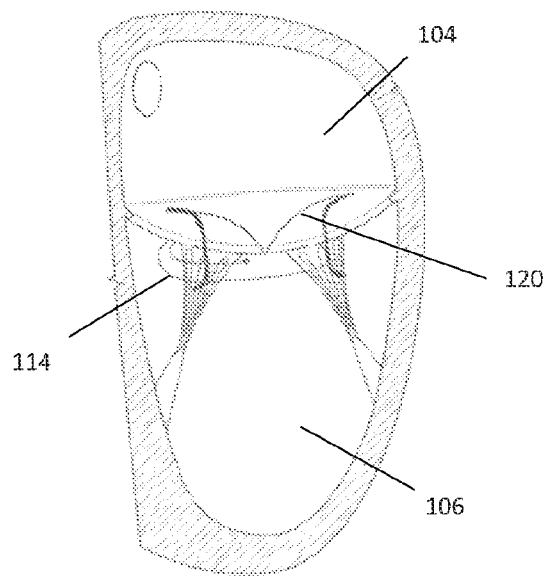

FIGS. 1A-1C depict a delivery system 2200 including an anchor guide 1000 configured in accordance with embodiments of the present disclosure. The anchor guide 1000 may form a portion of an anchor control catheter 122 (e.g., can be coupled with a distal portion of the anchor control catheter 122). Further, in some embodiments, the delivery system 2200 can include an outer sheath 108 configured to extend over the anchor control catheter 122 and/or the guide 1000.

Figure 6:
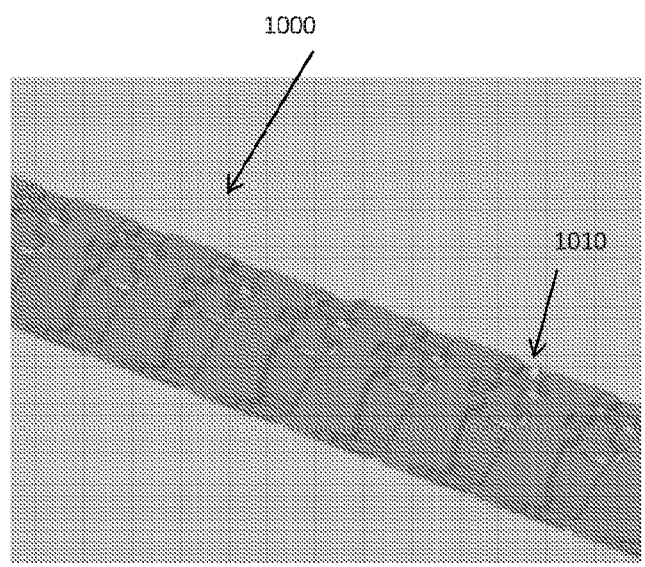
FIG. 6 shows a portion of an anchor guide including a toothed wedge cut.

In some embodiments, the anchor guide 1000 can be formed of a hypotube, such a hypotube having a plurality of slits or cuts 1010 therein (see FIG. 1B). The cuts 1010 can, for example, be formed using a laser cut pattern. In some embodiments, the cuts 1010 can be window cuts (for enhanced flexibility), interlocking spiral cuts (e.g., that enable a flexible configuration without compression and a rigid straight configuration when under compression), and/ or toothed wedge cuts (e.g., that enable a flexible configuration when not under compression and a rigid bent configuration whereby neighboring edges of the cuts 1010 engage or lock when under compression). An exemplary portion of a guide 1000 including toothed wedge cuts 1010 is shown in FIG. 6. The anchor guide 1000 can further include a spine (i.e., a continuous section extending an entire length of the guide 1000 that does not include any cuts therein).

In some embodiments, the anchor guide 1000 is configured to couple with, and be actuated by, one or more actuation elements (e.g., pullwires or cables). Actuation of the anchor guide 1000 with the more actuation elements may transition the anchor guide 1000 from a first configuration (e.g., that enables placement of the anchor guide 1000 within the outer sheath 108) to a second configuration (e.g., that is adapted to manipulate and position an anchor within the heart). As shown in FIG. 1B, for example, the anchor guide 1000 can include a first actuation element that terminates at a first termination point 1011 and a second actuation element that terminates at a second termination point 1012. The stiffness of the anchor guide 1000 can increase as the anchor guide 1000 transitions from the first configuration to the second configuration. The anchor guide 1000 in the second configuration can advantageously have a stiffness sufficiently high to deflect the anchor within the guide 1000 and to support and guide the anchor during delivery.

In some embodiments, the anchor guide 1000 may at least partially self-assemble, for example, using a shape memory effect. As used herein, self-assembly is a process in which a component transitions from a first configuration to a second configuration, without external application of force or direction. In some embodiments, the anchor guide 1000 may have a shape set geometry (e.g., via heat treatment) that is an intermediate geometry, e.g., a geometry that is in between the first configuration (e.g., straight) geometry and the second configuration (e.g., fully curved) geometry. The intermediate shape set geometry can reduce strain within the anchor guide 1000, for example, with respect to a strain induced by the first configuration and/or the second configuration geometry. By having an intermediate shape set that is between the first and second configurations, the strain in the anchor guide 1000 can be reduced as it transitions from the first configuration to the second configuration. For example, the anchor guide 1000 may have a (−) 3% strain in a specific region to obtain the first configuration and a (+) 3% strain to obtain the second configuration rather than 6% strain if shape set were at either of the end point configurations. The intermediate shape set geometry can further bias or urge the anchor guide 1000 to transition toward the second configuration from the first configuration as the anchor guide 1000 is deployed. The anchor guide 1000 may be formed of any of the materials described herein—for example, of a shape memory material (e.g., nitinol).

The anchor guide 1000 can include a plurality of sections 1001-1006 that may provide distinct features and/or functions for the anchor guide 1000 (e.g., during deployment of the anchor control catheter 122 and/or of the anchor). The anchor guide 1000 in the first configuration may be substantially straight or elongate (as shown in FIG. 1B) so as to fit within a delivery catheter. Once deployed in the heart, the anchor guide 1000 may assume the second configuration (as shown in FIG. 1A) and therefore take on a three-dimensional curved shape. When the anchor guide 1000 is in the second configuration, the distal section 1006 may be concentrically wrapped about and positioned above (superior to) a proximal section 1001 of the anchor guide 1000. Further, when the anchor guide 1000 is in the second configuration, the middle section 1003 may include an inversion. At times, the anchor guide 1000 may be referred to herein as an "inverted" anchor guide 1000.

Section 1001 can be the proximal-most section and can be configured to bond (e.g., thermally bond) to the distal portion of the anchor control catheter. Section 1001 can further include a plurality of window cuts (see FIG. 1B) therein to create enhanced flexibility. In some embodiments, the flexibility of section 1001 can be substantially equivalent to the flexibility of the anchor control catheter.

Section 1002, in turn, can include a plurality of aligned toothed wedge cuts 1010 having substantially equivalent lengths. The bending of section 1002 (towards the cuts) can be controlled by the first actuation element (that terminates at first termination point 1011) while the bending of the rest of the sections 1003-1006 can be controlled by the second actuation element (that terminates at the second termination point 1012). Because the bending of section 1002 is controlled by a separate actuation element from the rest of the sections, the bending section 1002 can be used to alter the planarity of the anchor 114 and/or guide 1000 during delivery of the anchor 114 (e.g., during encircling of the chordae).

Section 1003 can be configured as the inversion section (e.g., can include a u-shaped bend in the second configuration, such as a bend transitioning in direction through 160°-200°, such as 170°-190°, such as approximately 180°). In some embodiments, section 1003 can have an intermediate shapeset to reduce strain and/or to bias the section 1003 towards the desired curvature. Section 1003 can include a plurality of aligned toothed wedge cuts 1010 having substantially equivalent lengths. The toothed wedge cuts 1010 of section 1003 can be circumferentially offset (e.g., by approximately 90 degrees) from the toothed wedge cuts 1010 of section 1002.

Section 1004 can be a substantially straight section having a plurality of interlocking spiral cuts 1010. Section 1004 can be substantially rigid and straight with minimal compression in the second configuration and flexible in the first configuration (e.g., when no force is applied by the actuation element).

Section 1005 in the second configuration can have a twist along a curve that is tangent to the proximal section 1004 and/or to the distal end of section 1006. Section 1005 can include a plurality of toothed wedge cuts 1010 arranged in a spiral pattern and can further include an intermediate shapeset.

Finally, distal section 1006 can be configured to support and guide the anchor during encircling and/or valve deployment. The distal section 1006 in the second configuration can curve substantially in-plane and along the same axis as the anchor. Section 1005 can further include a plurality of aligned toothed wedge cuts 1010 of substantially equal length and can have an intermediate shapeset.

In some embodiments, the anchor guide 1000 can enable delivery of an anchor and a valve using a single catheter delivery system. For example, FIGS. 2A-2H show a method of delivering an anchor 114 and valve 120 using a single catheter prosthetic valve delivery system 3000. At FIG. 2A, the delivery system 3000 (including the anchor 114 and valve 120 therein) is translated over a wire 109 through a transseptal puncture and into an atrium 104 of a heart. At FIG. 2B, the wire 109 is retracted and an anchor control catheter 122 having an anchor guide 1000 at a distal end thereof is advanced into the atrium 104. The anchor guide 1000 may transition from a flexible first configuration to a rigid second configuration, where the second configuration includes an inverted portion such that a distal end 1115 thereof at least partially wraps concentrically about the delivery system 3000. At FIG. 2C, once the anchor guide 1000 is in the rigid second configuration, the anchor 114 is pushed out through distal tip of the anchor guide 1000, which urges the anchor 114 to wrap concentrically about the valve delivery system 3000. The mechanical properties (e.g., stiffness) and geometry (e.g., curvature) of the anchor guide 1000 can provide torque on the anchor 114 during deployment to enable the anchor 114 to deploy concentrically around the delivery system 3000 as the anchor 114 is released from the anchor guide 1000. In some embodiments, a proximal portion of the anchor 114 can remain partially within the distal tip of the anchor guide 1000 to provide additional control over the anchor 114 as the anchor 114 is placed. At FIG. 2D, the entire delivery system 3000 is pushed and steered (for example, via steering mechanisms in the outer sheath 108) across the mitral annulus and toward an apex of the ventricle 106. In some embodiments, counter-rotation of the anchor 114 (via counter-rotation of anchor control catheter 122 and the anchor guide 1000) may aid in advancing the anchor 114 across the mitral valve without entanglement of the chordae. At FIG. 2E, the anchor 114 has been positioned at a selected depth within the ventricle 106, and forward (e.g., clockwise) rotation of the anchor 114 (via forward rotation of the anchor control catheter 122 and the anchor guide 1000) enables the anchor 114 to encircle the mitral leaflets and chordae. The selected depth of the anchor 114 may be in close proximity to the surface of the annulus, within the ventricle 106. In some embodiments, the anchor 114 placement and encircling is as close to the annulus as can be achieved. In some embodiments, an inverted anchor guide 1000 may advantageously transmit forces to the anchor 114 via the anchor control catheter 122 that urge the anchor 114 toward the annulus and/or maintain anchor planarity during encirclement. For example, the inverted anchor guide 1000 can transmit a pushing force toward the sub-annular space of the ventricle 106, via a pulling force generated at the anchor control catheter 122. Once the anchor 114 has been placed in a selected position about the chordae and/or leaflets, a prosthetic valve 120 may be deployed by retraction an outer sheath 108 of the valve delivery system 3000 (e.g., FIG. 2F). In some embodiments, deployment of the prosthetic valve 120 is performed while the anchor guide 1000 maintains a selected position of the anchor 114. In some embodiments, the position of the anchor guide 1000 and/or anchor 114 can be adjusted during and/or following deployment of the prosthetic valve 120 (e.g., by torquing or otherwise moving the anchor guide 1000 while the anchor guide 1000 is in the rigid configuration). At FIG. 2G, the anchor 114 is released from the valve delivery system 3000 and the anchor control catheter is proximally retracted. At FIG. 2H, the valve delivery system 3000 is retracted from the heart with the prosthetic valve 120 and anchor 114 remaining implanted.

Figure 3E:
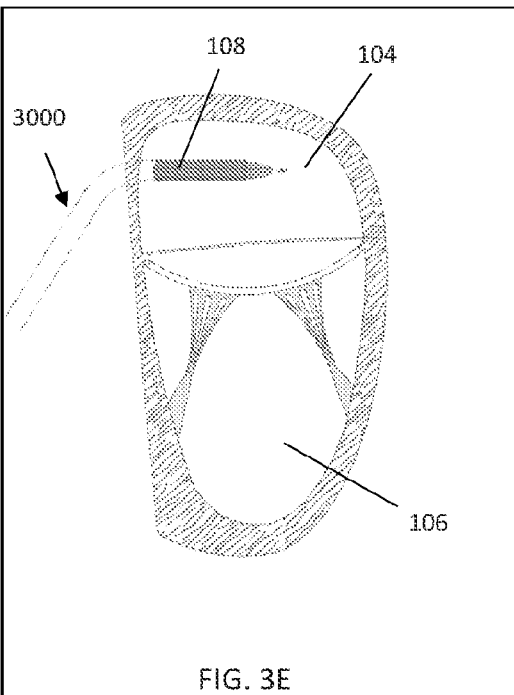
FIGS. 3A-3X show an embodiment of a method of delivering an anchor and a valve prosthesis near a native valve annulus using an inverted guide and a single valve delivery catheter.
Figure 3F:
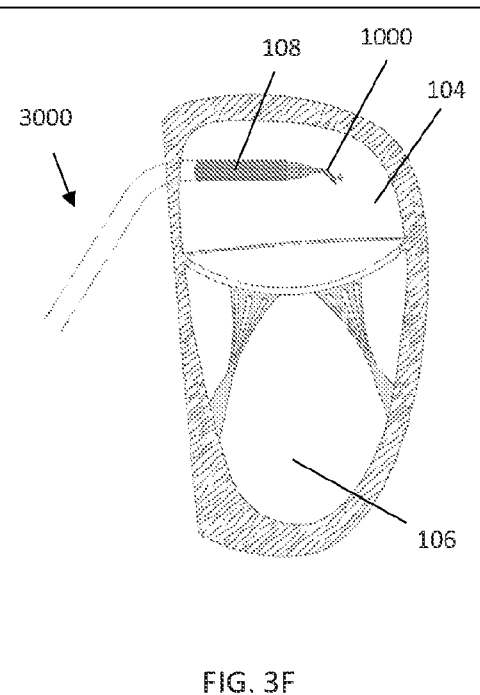
Figure 3G:
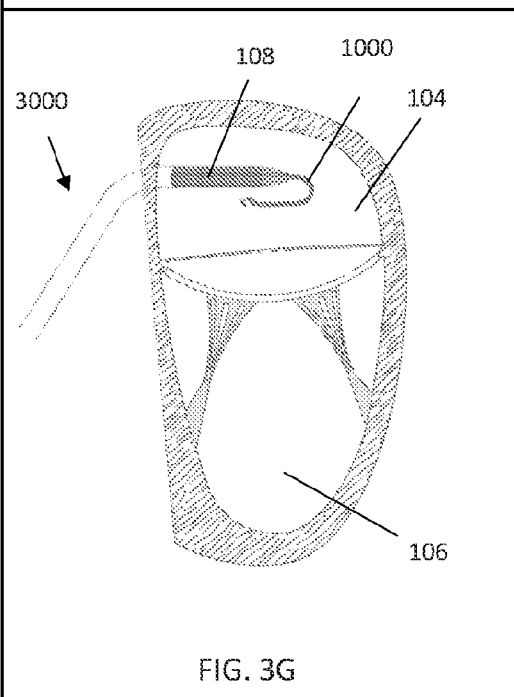
Figure 3H:
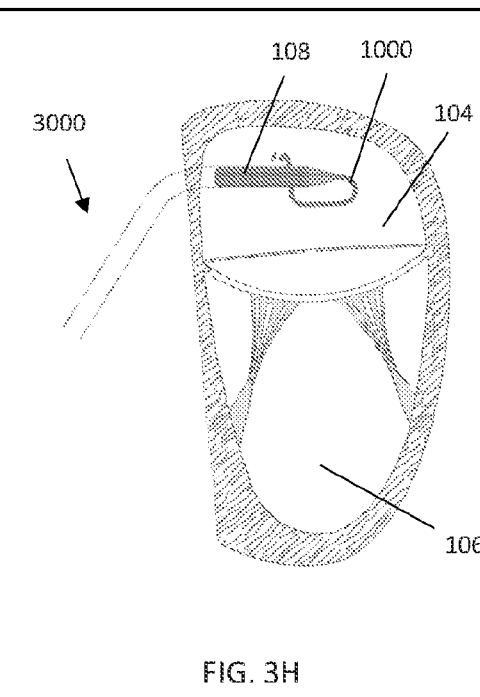
Figure 3U:
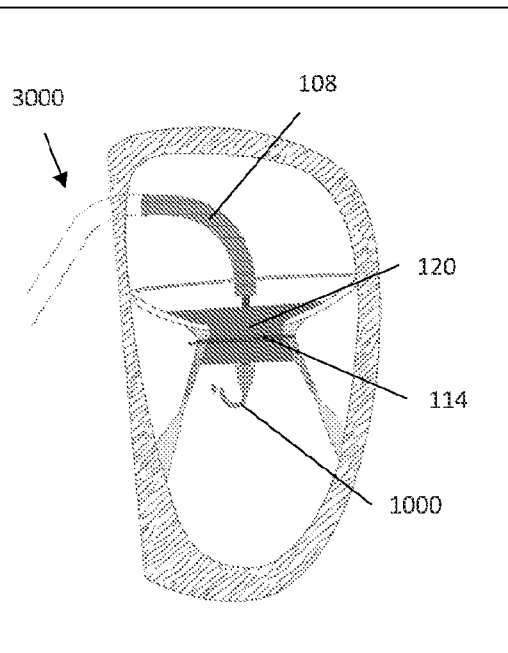
Figure 3V:
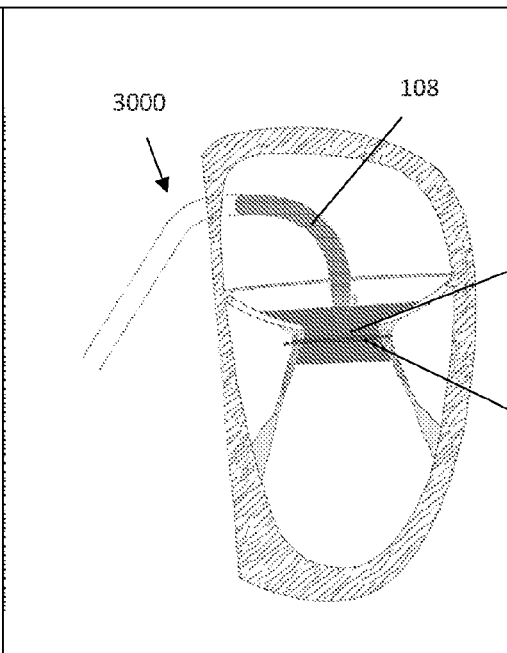
Figure 3W:
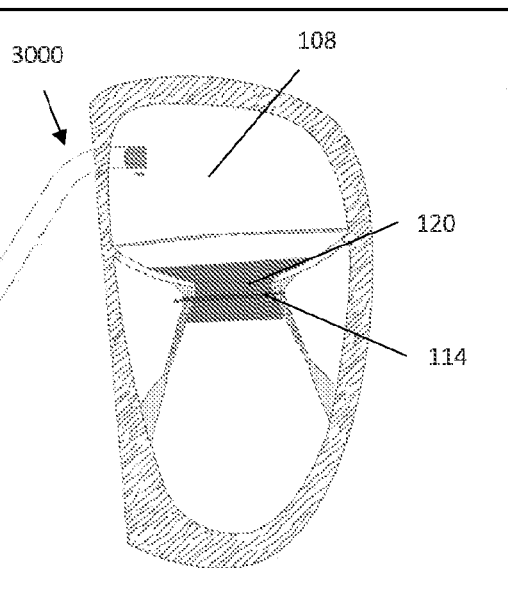
Figure 3X:
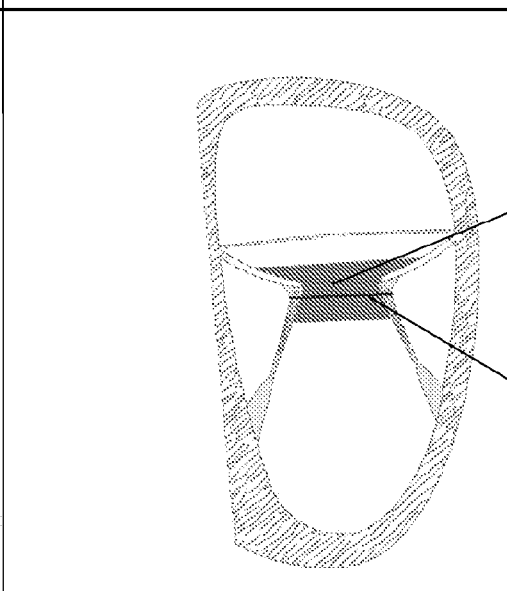
Figure 4A:
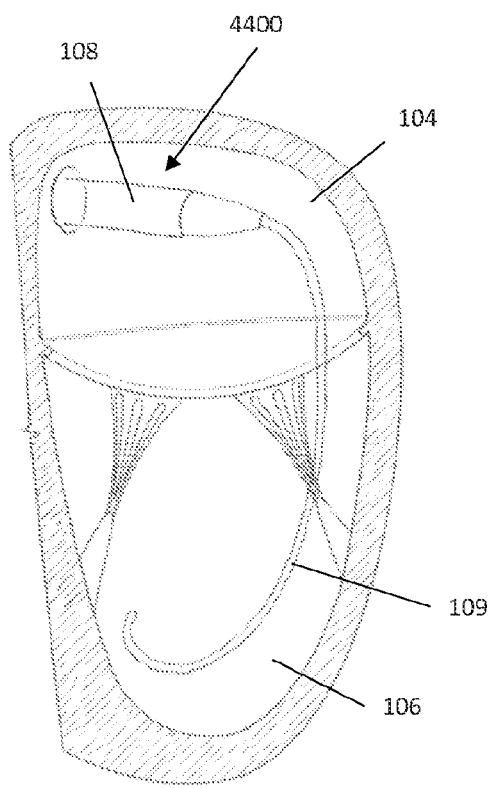
FIGS. 4A-K shown embodiment of a method of delivering an anchor and valve prosthesis near a native valve annulus using an anchor delivery catheter with an inverted guide and a separate valve delivery catheter.
Figure 4B:
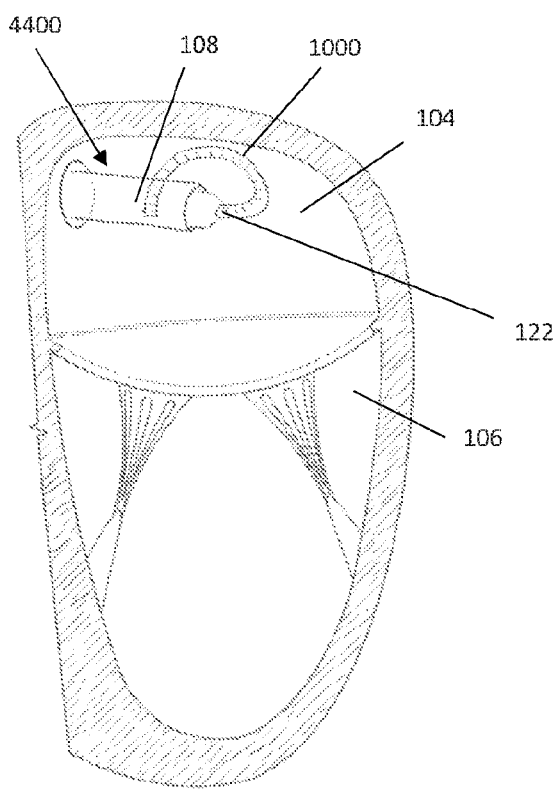
Figure 4C:
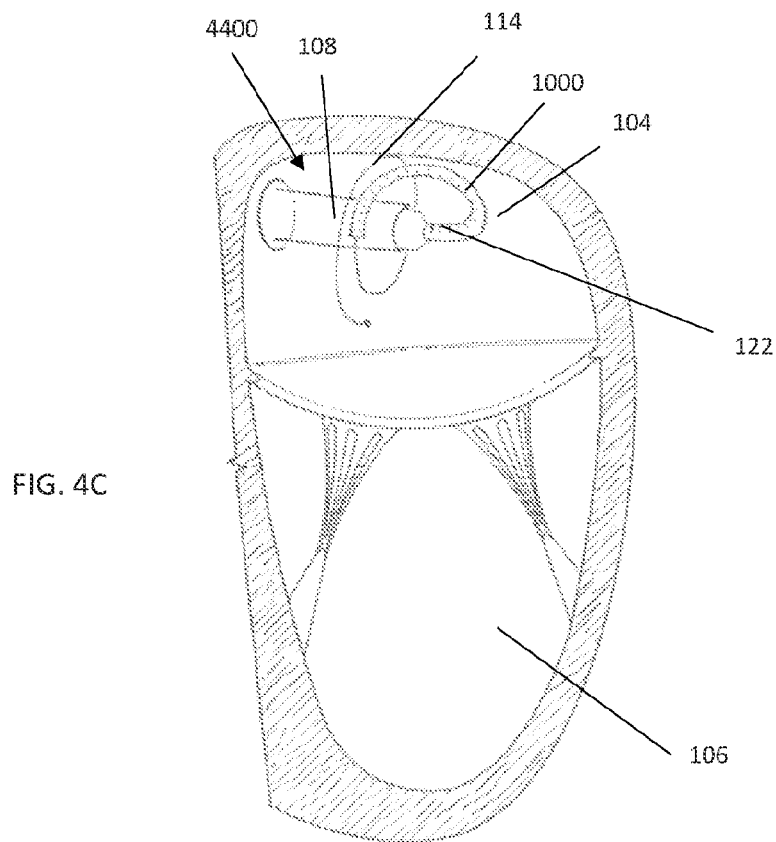
Figure 4D:
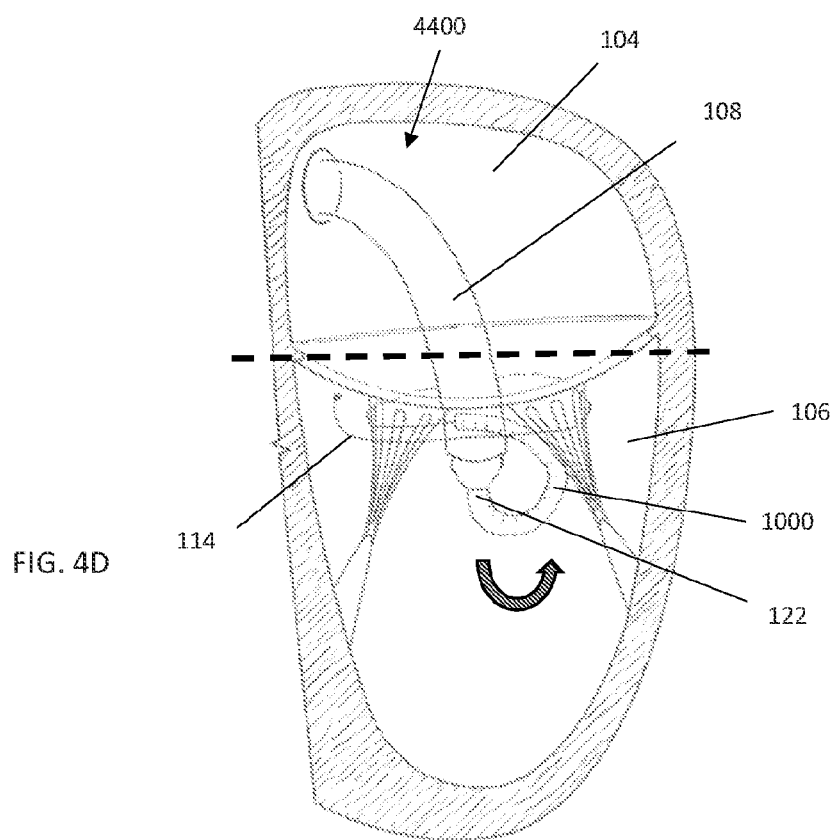
Figure 4E:
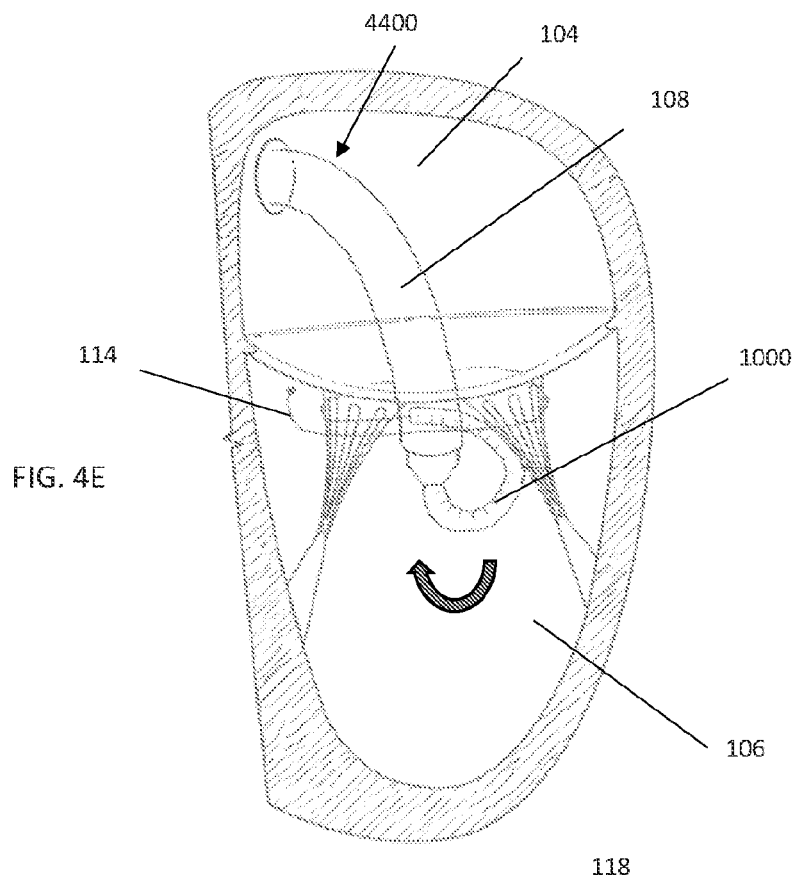
Figure 4F:
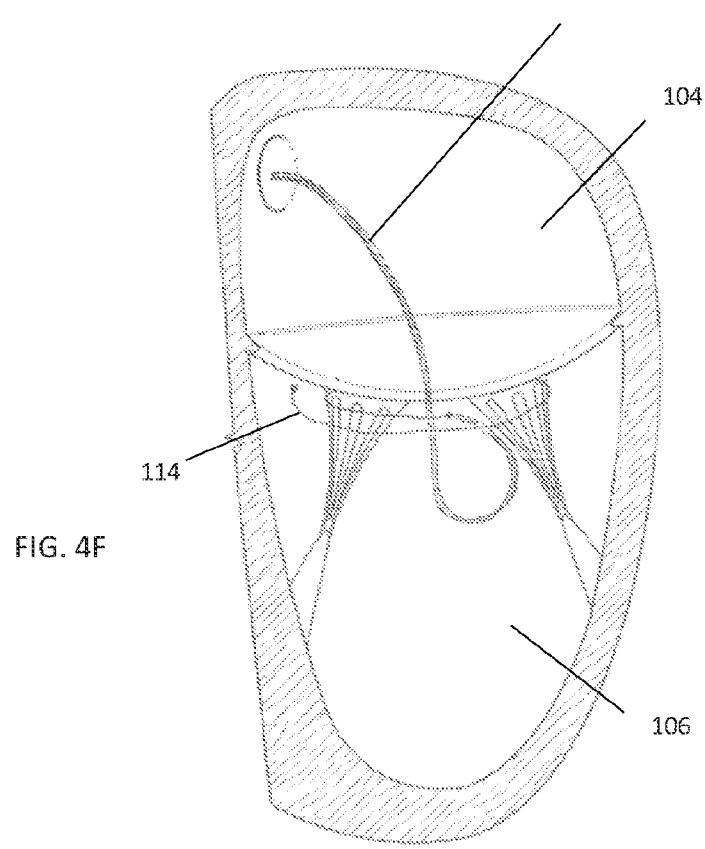
Figure 4G:
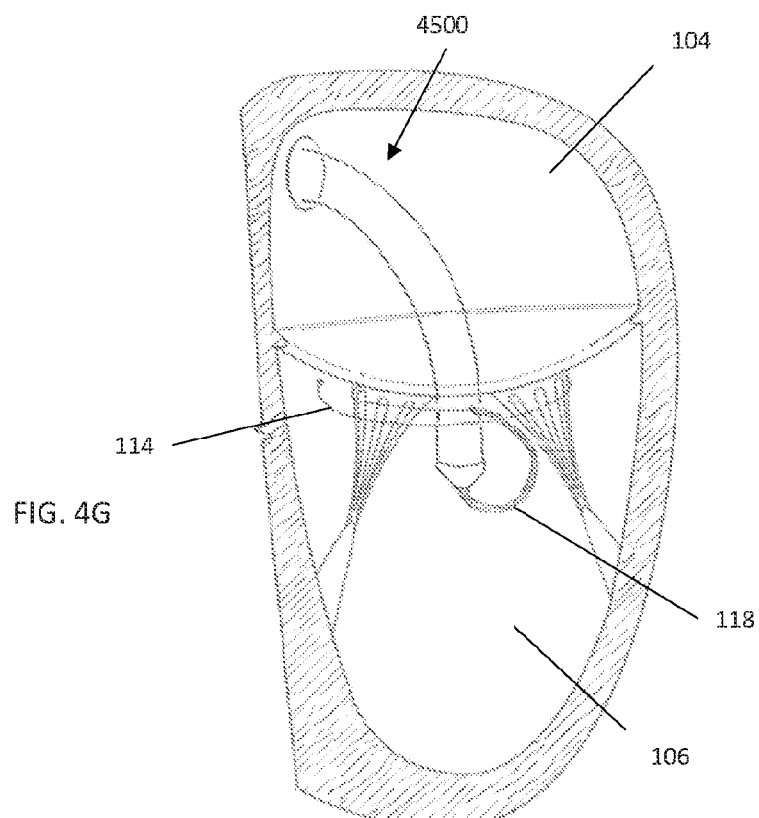
Figure 4H:
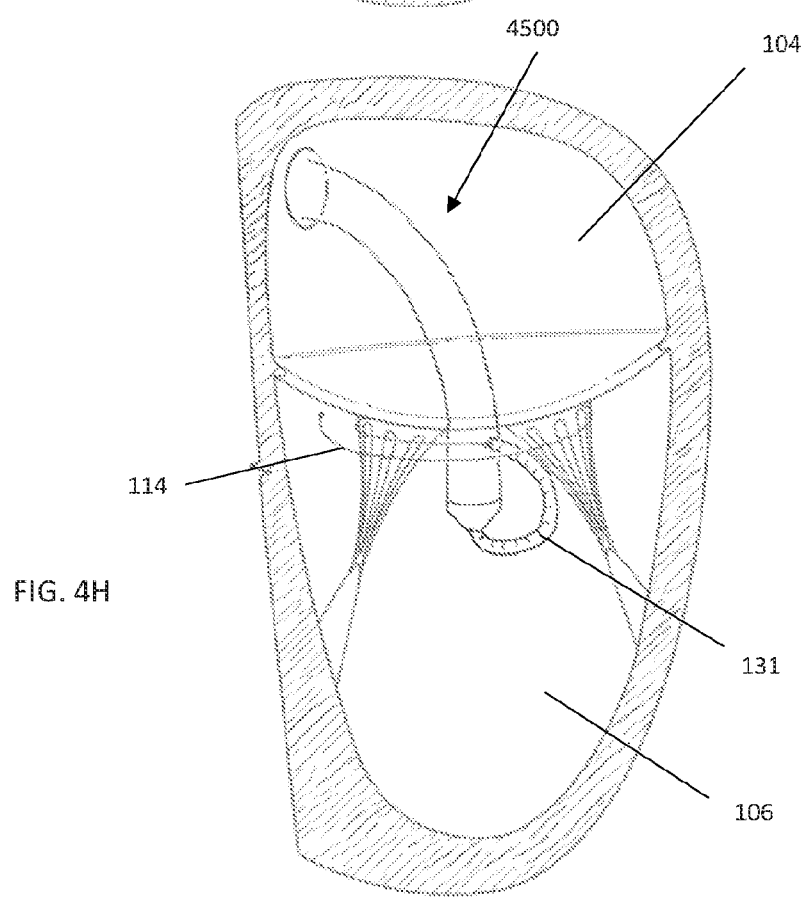
Figure 4I:
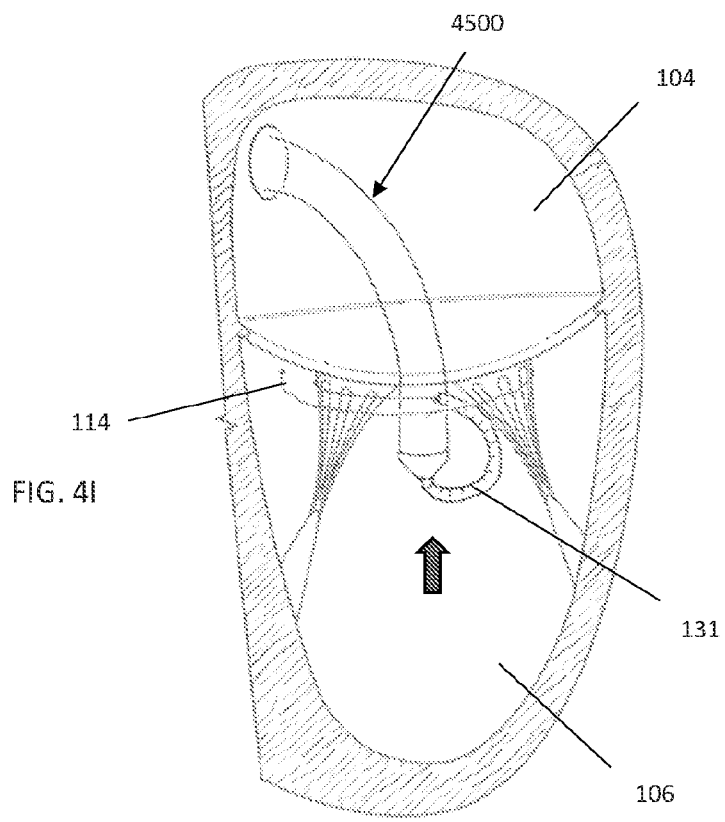
Figure 4J:
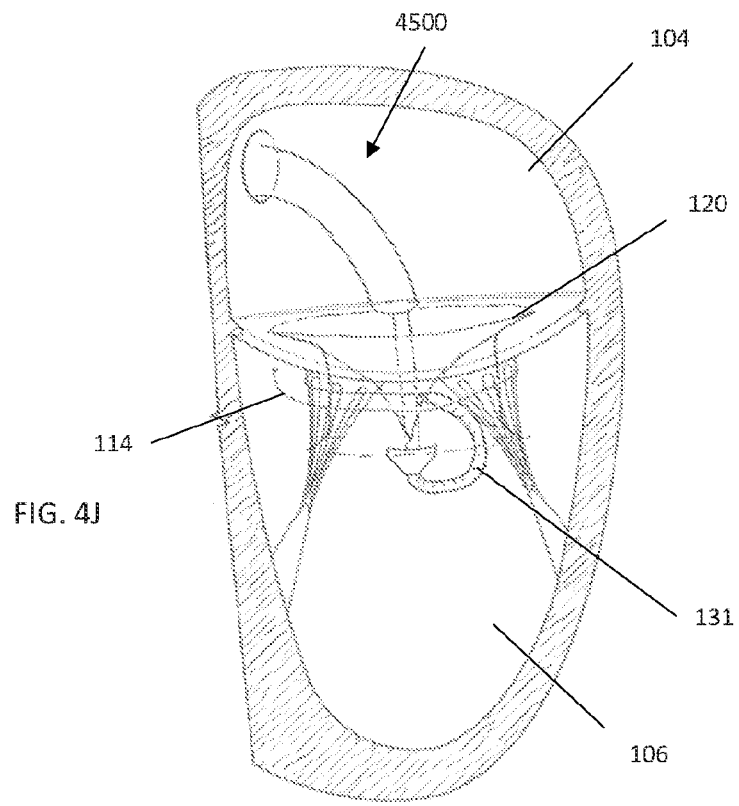
Figure 4K:
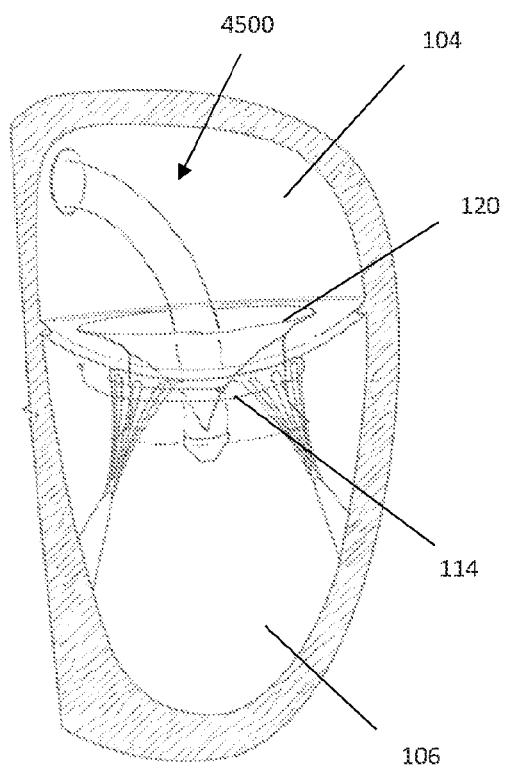

FIGS. 3A-3X depict a more detailed example of deploying a prosthetic valve to a heart using a single catheter delivery system 3000 with guide 1000. At FIG. 3A, the wire 109 can be placed through a transseptal puncture into the atrium 104 and/or ventricle 106. At FIGS. 3B and 3C, the delivery system 3000 can be translated over the wire 109 into the atrium 104. At FIGS. 3D and 3E, the wire 109 can be retracted. At FIG. 3F, the anchor guide 1000 can be advanced out of the outer sheath 108 and into the atrium 104. At FIG. 3G, the anchor guide 1000 can be further advanced out of the outer sheath 108 and begin to invert (e.g., due to self-assembly). At FIG. 3H, the anchor guide 1000 can be completely advanced out of the outer sheath 108 and transitioned fully from the first configuration to the inverted and rigidized second configuration (e.g., via self-assembly and/or activation of the actuation elements). At FIGS. 3I-3K, the anchor 114 can be advanced out of the anchor guide 1000. At FIG. 3L, the delivery system 3000 can then be advanced so as to move the anchor 114 and the anchor guide 1000 into the ventricle 106. In some embodiments, the anchor guide 1000 can be counter-rotated as the delivery system 3000 is advanced so as to prevent the anchor 114 and/or guide 1000 from entangling with the chordae. At FIGS. 3M-3N, the anchor guide 1000 can be rotated so as to rotate the anchor 114 around the chordae 114. At FIGS. 3O and 3P, the anchor guide 1000 (still in the rigid configuration) can be torqued or otherwise maneuvered so as to adjust the planarity and/or positioning of the anchor 114 (e.g., so as to push the anchor 114 close to the mitral valve annulus). At FIGS. 3Q-3T, the valve 120 can be released within the anchor 114 by retracting the sheath 108 proximally. At FIG. 3U, the anchor guide 1000 can be transitioned back to the flexible configuration and pulled within the delivery system 3000. At FIGS. 3V-3X, the delivery system 3000 can then be fully removed from the heart, leaving the anchor 114 and valve 120 in place.

Advantageously, the anchor guide 1000 can enable use of a single catheter delivery system 3000 while also ensuring anchor planarity and positioning control. That is, because the anchor guide 1000 can be inverted within the ventricle 104, the valve prosthesis 120 can be positioned radially within, and axially aligned relative to, the anchor 114 while the anchor guide 1000 remains in position. Further, the anchor guide 1000 can be used to specifically and accurately adjust the planarity and position of the anchor 114 both before, during, and after deployment of the prosthetic valve. The anchor guide 1000 can advantageously be relatively flexible in the first (non-actuated) configuration and relatively rigid in the second (actuated) configuration for enhanced control of the anchor 114. The anchor guide 1000 in the second configuration can advantageously both provide support to the anchor 114 during encircling of the anchor 114 and can hold the anchor 114 in the correct location for valve deployment when a single catheter delivery system 3000 is used.

In some embodiments, the anchor guide 1000 can be part of a double catheter delivery system (e.g., a delivery system that includes a catheter for delivery of the anchor and a separate catheter for delivery of the frame). For example, FIGS. 4A-4K show a method of delivering an anchor 114 and valve 120 using a double catheter prosthetic valve delivery system. At FIG. 4A, an anchor delivery catheter 4400 is tracked over a wire 109 through a transseptal puncture into an atrium 104 of the heart. At FIG. 4B, the wire 109 can be removed and an anchor control catheter 122 (with guide arm 1000 at the distal end thereof) can be advanced through the outer sheath 108 until the guide arm 1000 is deployed in the atrium 104 and transitioned fully from the first configuration to the second configuration. At FIG. 4C, the anchor 114 can be deployed through the lumen in the guide arm 1000 such that the anchor 114 wraps concentrically around the anchor delivery catheter 4400. At FIG. 4D, the anchor delivery catheter 4400 and anchor 114 can be pushed and/or steered across the mitral annulus into the ventricle 106. In some embodiments, counter-rotation of the anchor 114 (via counter-rotation of the anchor control catheter 122 and the anchor guide 1000) may aid in advancing the anchor 114 across the mitral valve without entanglement of the chordae. At FIG. 4E, the anchor 114 can be positioned such that the distal tip is in the LVOT, and then the anchor 114 can be rotated (via rotation of the anchor control catheter 122 and the anchor guide 1000) such that the tip travels between the ventricular walls and the leaflets/chordae. At FIG. 4F, the anchor guide 1000 can be retracted such that an inverted loop of tether 118 is left attached to the anchor 114. The anchor delivery catheter 4400 can be completely removed from the patient, leaving only the anchor 114 and tether 118 in position. At FIG. 4G, a valve delivery catheter 4500 can be tracked concentrically over the tether 118. At FIG. 4H, a positioning tool 131 can be deployed through the valve delivery catheter 4500 over the tether 118. A distal end of the positioning tool 131 can engage with a proximal end of the anchor 114, causing the positioning tool 114 to become stiff and holding the anchor 114 in a specific orientation. At FIG. 4I, the positioning tool 114 can be manipulated such that the anchor 114 is lifted higher into the sub-annular space, and the valve delivery catheter 4500 can be manipulated so as to be at the desired deployment height relative to the anchor 114. At FIG. 4J, the valve 120 can be deployed (e.g., by retracting an outer sleeve of the valve delivery catheter). At FIG. 4K, the tether 118 can be released from the anchor 114, the tether 118 and positioning tool 131 can be retracted into the valve delivery catheter 4500, the outer sleeve can be advanced, and the entire valve delivery system 4500 can be removed from the patient.

The anchor guide 1000 can advantageously be relatively flexible in the first (non-actuated) configuration and relatively rigid in the second (actuated) configuration for enhanced control of the anchor 114. Advantageously, the anchor guide 1000 in the second configuration can be used as part of a double catheter delivery system to precisely control placement of the anchor 114 prior to delivery (e.g., as a result of the specific shape and stiffness of the anchor guide 1000 in the second configuration). Further, the anchor guide 1000 in the second configuration can provide support to the anchor during encircling. The bends or curves of the anchor guide 1000 in the second configuration can additionally advantageously be fully inside the ventricle (below the leaflets) during encircling instead of in the intra-annular space, thereby preventing the anchor guide 1000 from interfering with the functioning of the leaflets. Additionally, the anchor guide 1000, because it leaves a tether 118 inverted and concentrically placed within the anchor 114, can advantageously enable concentric delivery of the valve 120 therethrough.

Figure 5A:
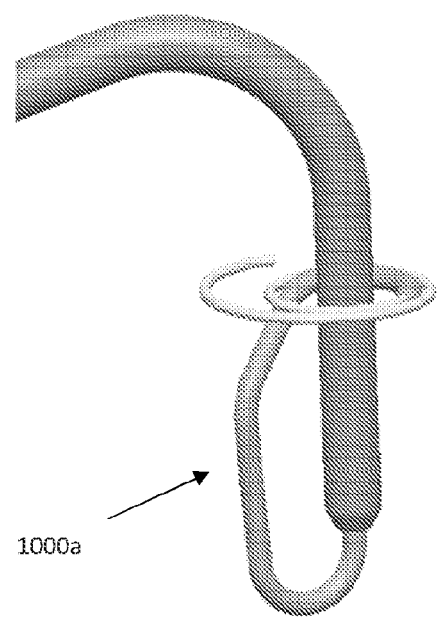
FIG. 5A shows an inverted anchor guide for use with a single catheter delivery system.
Figure 5B:
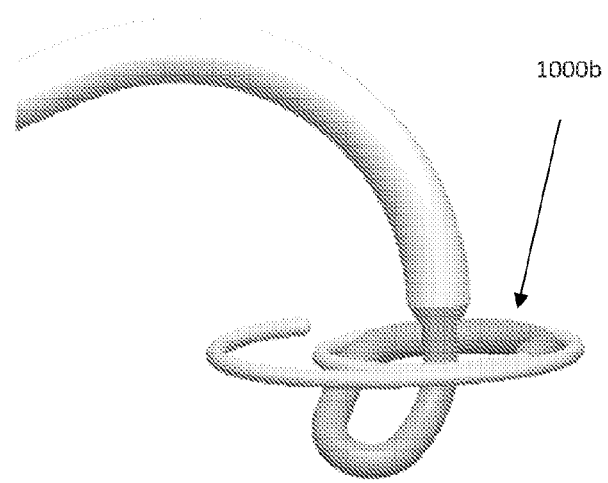
FIG. 5B shows an inverted anchor guide for use with a double catheter delivery system.

In some embodiments, an inverted anchor guide for use with a single catheter delivery system can be slightly different in configuration and design from an inverted anchor guide for use with a double catheter delivery system. For example, as shown in FIGS. 5A-5B, the anchor guide 1000a for use with a single catheter delivery system can have a longer total axial length than the anchor guide 1000b for use with a double catheter delivery system. For example, any or all of sections 1001-1005 can be longer for the single catheter delivery system than the double catheter delivery system. The longer total length of the anchor guide 1000a for the single catheter delivery system can advantageously accommodate placement of the valve within the anchor/annulus while the shorter length of the anchor guide 1000b for the double catheter delivery system can advantageously provide enhanced control over the anchor (e.g., by shortening the moment arm relative to the anchor).

Although described herein as being actuated by one or more actuation elements such as pullwires or cables, it should be understood that other actuating mechanisms are possible. For example, a concentric actuation mechanism can be used whereby an inner shaft can be pulled proximally relative to the anchor guide 1000 to transition the anchor guide 1000 from the first configuration to the second configuration (e.g., as described with respect to FIGS. 11A-11B). As another example, an outer sleeve can be pulled proximally relative to the anchor guide 1000 to transition the anchor guide 1000 from the first configuration to the second configuration.

Another exemplary anchor guide 2000 is shown in FIGS. 7A-7I. The anchor guide 2000 can be similar to anchor guide 1000, but without the presence of an inversion. Like anchor guide 1000, anchor guide 2000 can be formed of a hypotube, such as a hypotube having a plurality of slits or cuts 2010 therein (see FIGS. 7A, 7C, 7D, and 7I). In some embodiments, the cuts 2010 can be window cuts (for enhanced flexibility), interlocking spiral cuts (e.g., that enable a flexible configuration without compression and a rigid straight configuration when under compression), and/or toothed wedge cuts (e.g., that enable a flexible configuration when not under compression and a rigid bent configuration whereby neighboring edges of the cuts 2010 engage or lock when under compression).

Figure 11A:
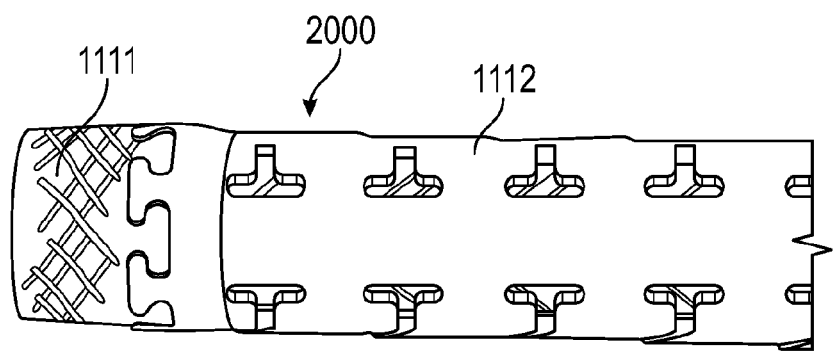
FIGS. 11A-11B show a concentric actuation mechanism for an anchor guide.
Figure 11B:
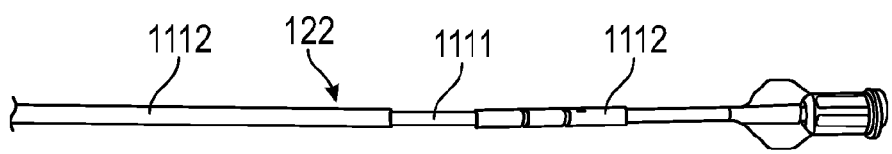

In some embodiments, the anchor guide 2000 is configured to couple with, and be actuated by, one or more actuation elements (e.g., via a concentric actuation member as described with respect to FIGS. 11A-11B). Actuation of the anchor guide 2000 with the one or more actuation elements may transition the anchor guide 2000 from a first configuration (e.g., that enables placement of the anchor guide 2000 within an outer sheath 108) shown in FIG. 7A to a second configuration (e.g., that is adapted to manipulate and position an anchor within the heart) shown in FIGS. 7B-7I. Like anchor guide 1000, the stiffness of the anchor guide 2000 can increase as the anchor guide 2000 transitions from the first configuration to the second configuration. The anchor guide 2000 in the second configuration can advantageously have a stiffness sufficiently high to deflect the anchor 114 within the guide 2000 and to support and guide the anchor 114 during delivery.

Figure 10A:
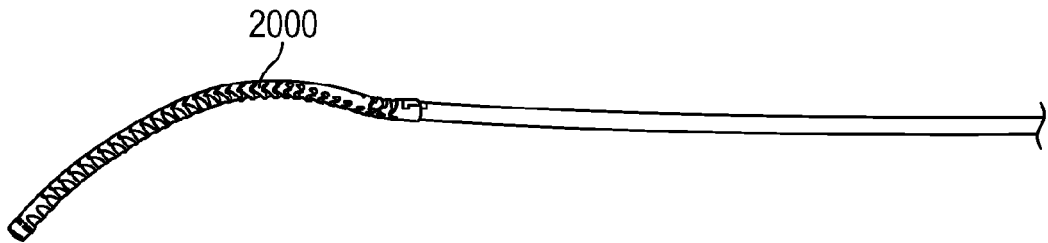
FIG. 10A shows an intermediate geometry shape set of an anchor guide.
Figure 10B:
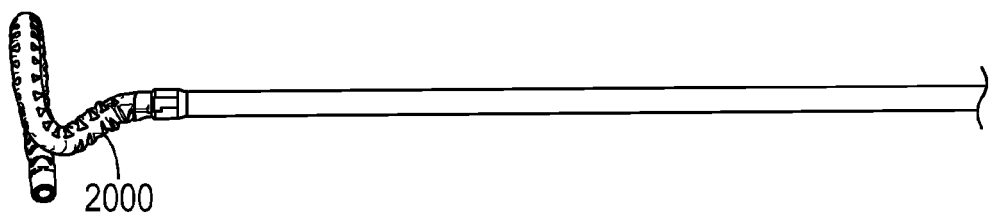
FIG. 10B shows the anchor guide of FIG. 10A in the deployed configuration.

In some embodiments, the anchor guide 2000 may at least partially self-assemble, for example, using a shape memory effect. In some embodiments (and as shown in FIG. 10A), the anchor guide 2000 may have a shape set geometry (e.g., via heat treatment) that is an intermediate geometry, e.g., a geometry that is in between the first configuration (e.g., straight) geometry and the second configuration (e.g., fully curved) geometry (as shown in the transition from FIGS. 10A-10B). The intermediate shape set geometry can reduce strain within the anchor guide 2000, for example, with respect to a strain induced by the first configuration and/or the second configuration geometry. By having an intermediate shape set that is between the first and second configurations, the strain in the anchor guide 2000 can be reduced as it transitions from the first configuration to the second configuration. For example, the anchor guide 2000 may have a (−) 3% strain in a specific region to obtain the first configuration and a (+) 3% strain to obtain the second second configuration rather than 6% strain if shape set were at either of the end point configurations. The intermediate shape set geometry can further bias or urge the anchor guide 2000 to transition toward the second configuration from the first configuration as the anchor guide 2000 is deployed. The anchor guide 2000 may be formed of any of the materials described herein—for example, of a shape memory material (e.g., nitinol).

Figure 7E:
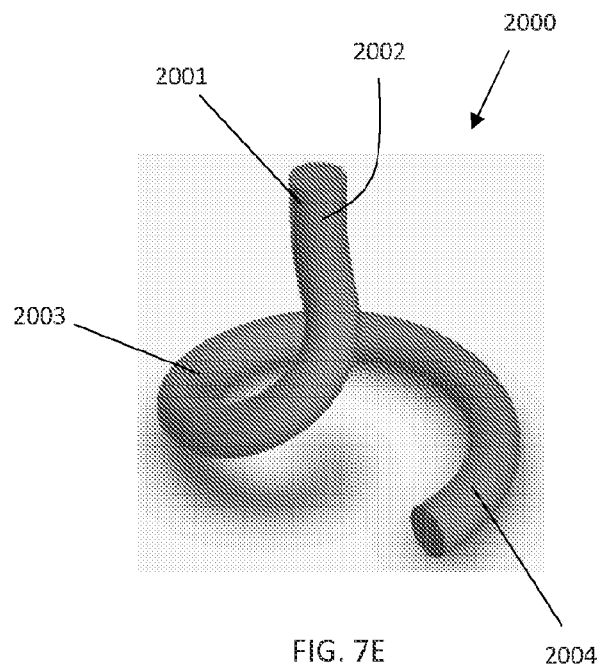
Figure 7F:
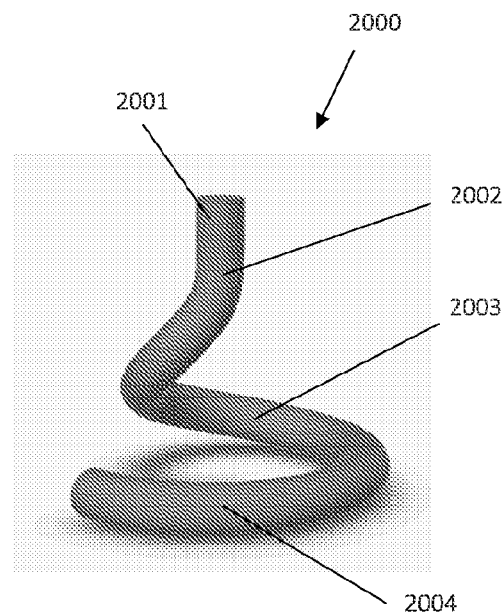
Figure 7G:
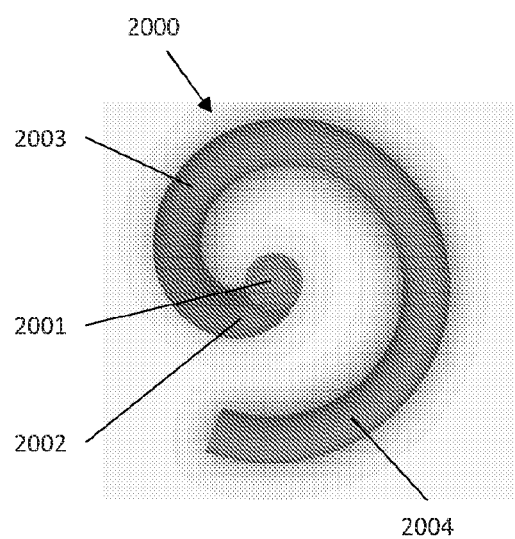
Figure 7H:
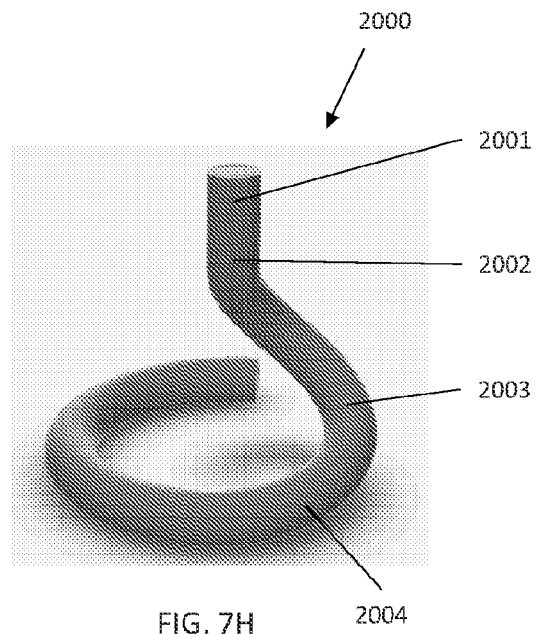
Figure 71:
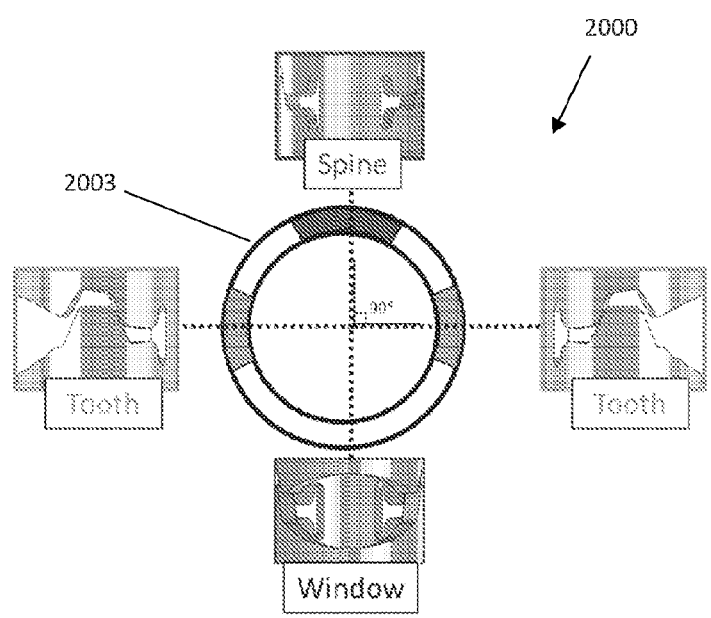

The anchor guide 2000 can include a plurality of sections 2001-2004 that may provide distinct features and/or functions for the anchor guide 2000 (e.g., during deployment of the anchor control catheter and/or of the anchor). The anchor guide 2000 in the first configuration may be substantially straight or elongate (as shown in FIG. 7A) so as to fit within a delivery catheter. Once deployed in the heart, the anchor guide 2000 may assume the second configuration (as shown in FIGS. 7B-7I) and therefore take on a three-dimensional curved shape. When the anchor guide 2000 is in the second configuration, the distal section 2004 may be concentrically wrapped about an axis 2005 that extends through the proximal section 2001. Unlike anchor guide 1000, the distal section 2004 of anchor guide 2000 in the second configuration can remain distal of the proximal section 2001 and can form the distal-most portion of the deployed anchor guide 2000.

Figure 13A:
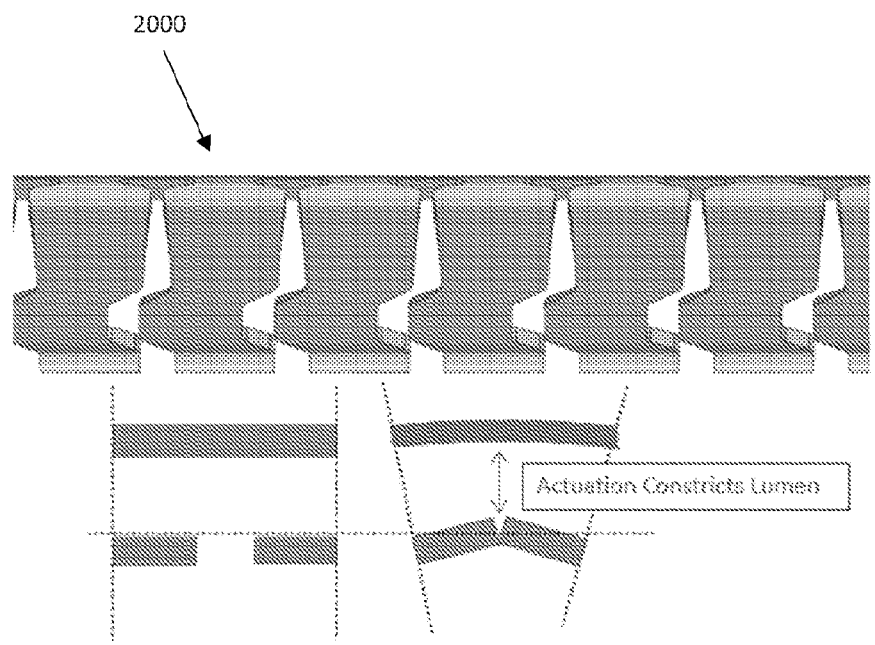
FIGS. 13A-13B show a comparison of the effects of a cut pattern without curved window cuts (FIG. 13A) to the effects of a cut pattern with curved window cuts (FIG. 13B).
Figure 13B:
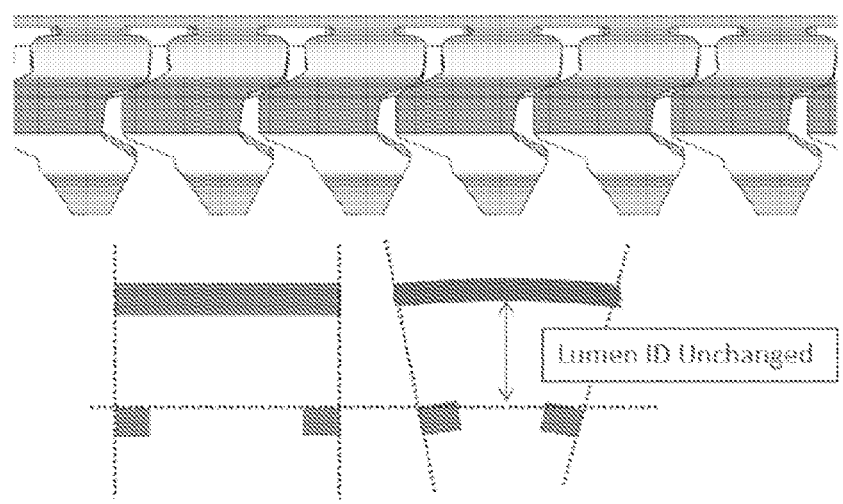

Proximal section 2001 can be the proximal-most section and can be configured to bond (e.g., thermally bond) to the distal portion of the anchor control catheter 122. Section 2001 can be substantially straight and axially aligned with a distal end of the anchor control catheter 122. Sections 2002-2004 can all include a spine, a plurality of window cuts (e.g., to reduce friction with the concentric actuation member), and a plurality of toothed wedge cuts (e.g., trapezoidal cuts) to create hard stops to form the final shape (e.g., the second configuration). The cross-section of section 2003 is shown in FIG. 7I. As shown in FIG. 7I, the anchor guide 2000 can include the spine at a first circumferential location (e.g., at 0°), a toothed wedge cut at a second circumferential location (e.g., at 90°), a window cut at a third circumferential location (e.g., at 180°), and another toothed wedge cut at a fourth circumferential location (e.g., at 270°). Referring to FIGS. 13A-13B, having an anchor guide 2000 with window cuts in combination with the toothed wedge cuts (shown in FIG. 13B) can advantageously reduce the amount of constriction in the central lumen of the anchor guide 2000 when the anchor guide is in the rigid configuration relative to an anchor guide without the window cuts (shown in FIG. 13A). The reduction in lumen constriction can advantageously decrease the force for actuation of the anchor guide 2000 from the flexible to the rigid configuration, which can in turn reduce the amount of whipping or degradation caused to the anchor control catheter 122. Further, the reduction in lumen constriction can advantageously reduce friction as the anchor 114 passes through the anchor guide 2000. Finally, having an anchor guide 2000 with window cuts can also advantageously provide clearance for edge treatments (e.g., rounding processing) and/or internal coating or lamination steps, during manufacturing of the anchor guide 2000, which can further help reduce friction as the anchor 114 passes through the anchor guide 2000.

Additionally, each of sections 2002-2004 can have a respective intermediate shape set. Section 2002 can include a plurality of axially aligned cuts and can be configured to curve away axially and radially away from the straight section 2001. Section 2003 can include a plurality of cuts arranged in a spiral pattern such that section 2003 takes on a three-dimensional spiral in the second configuration. Finally, distal section 2004 can include a plurality of axially aligned cuts configured such that section 2004 takes on a flat or planar curve that is concentric with the axis 2005 of section 2001 and that arcs through approximately 150-210 degrees, such as 180 degrees (e.g., so as to hold 180 degrees of the spiral anchor 114 therein). The distal section 2004 can further be positioned within a plane that is perpendicular to the axis 2005 of the proximal section 2001.

Figure 8A:
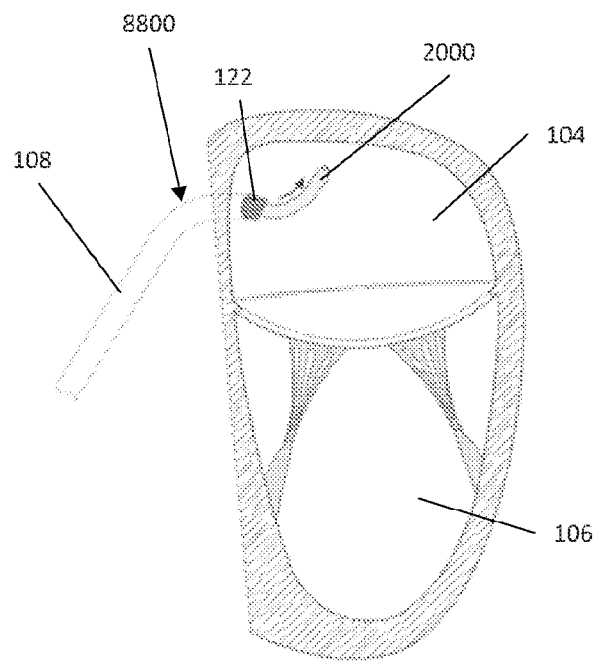
FIGS. 8A-8M show an embodiment of a method of delivering an anchor using an anchor guide similar to that shown in FIGS. 7A-7I.
Figure 8B:
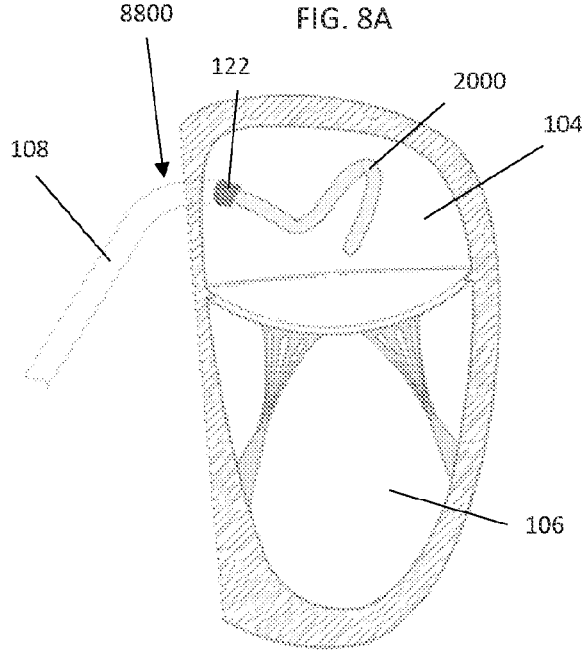
Figure 8C:
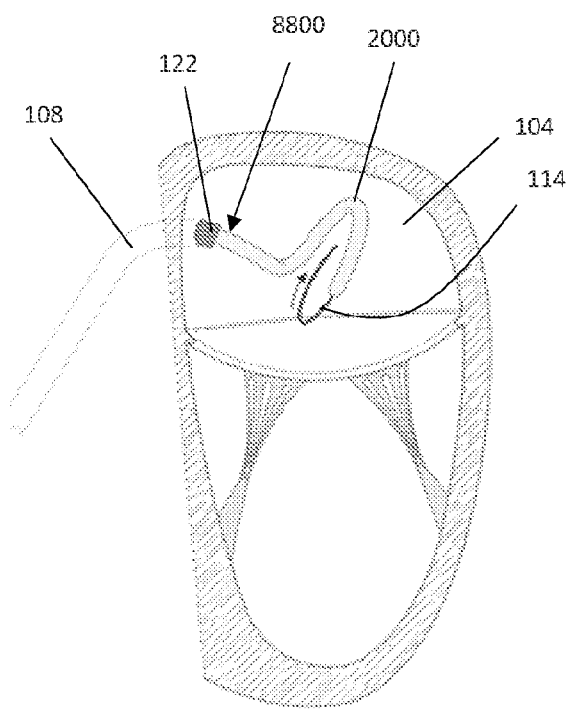
Figure 8D:
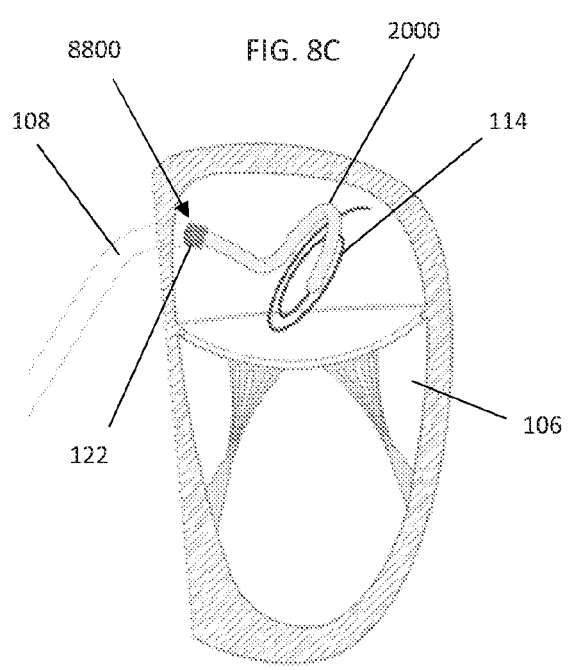
Figure 8E:
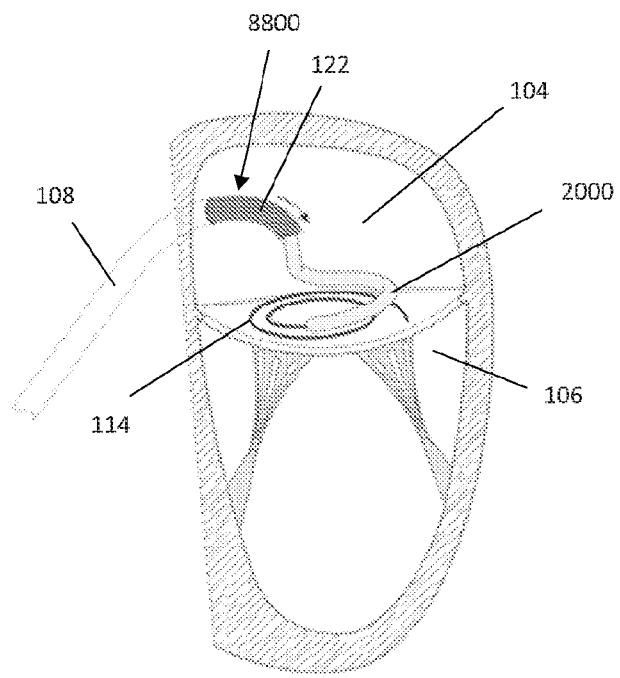
Figure 8F:
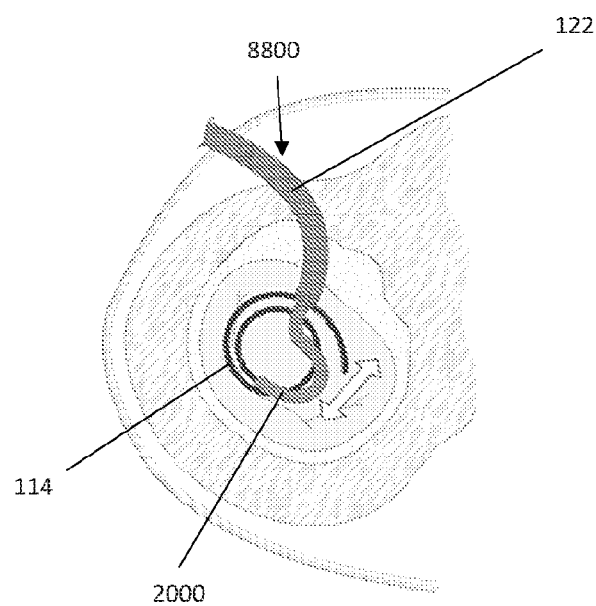
Figure 8G:
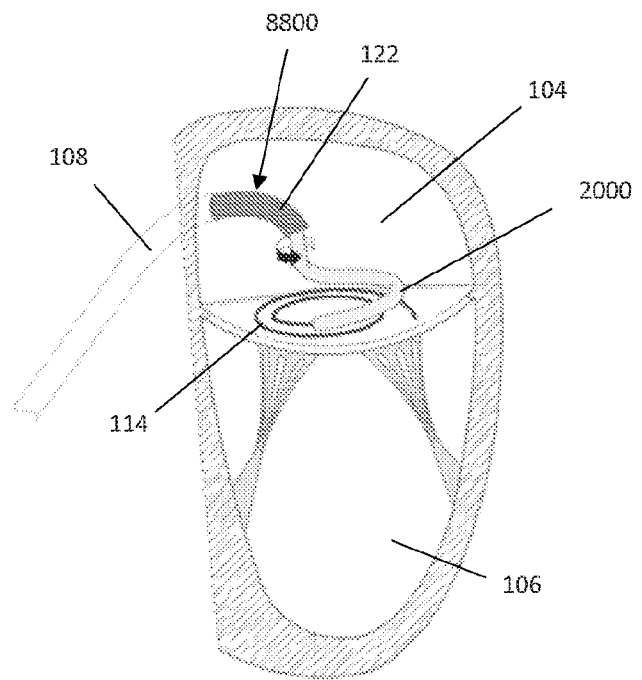
Figure 8H:
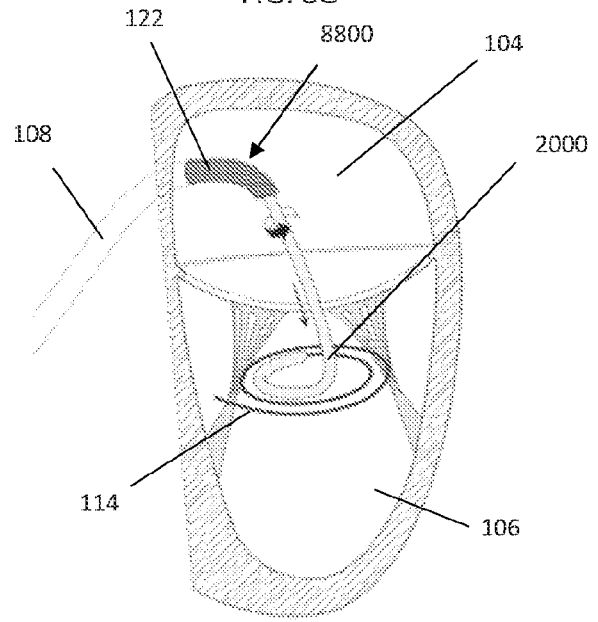
Figure 8I:
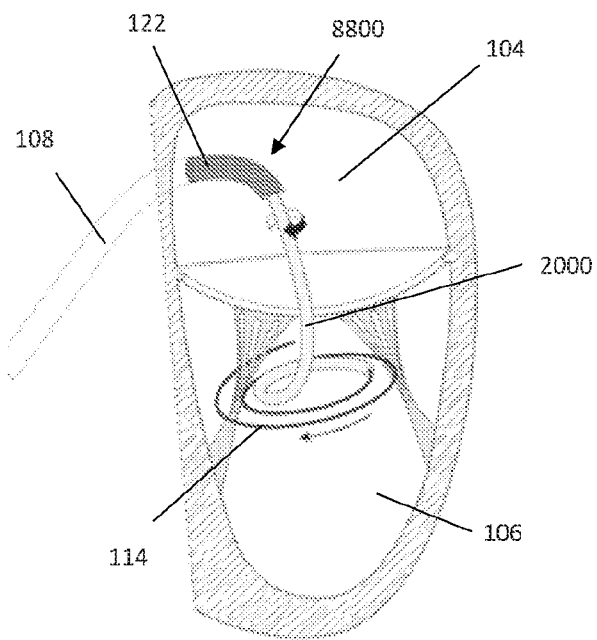
Figure 8J:
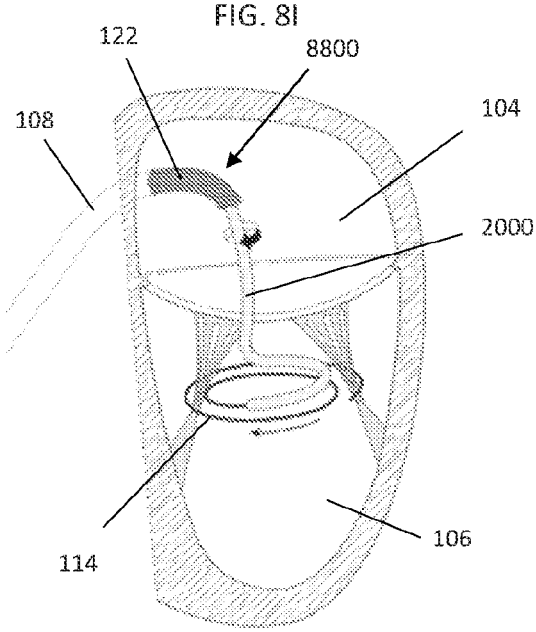
Figure 8K:
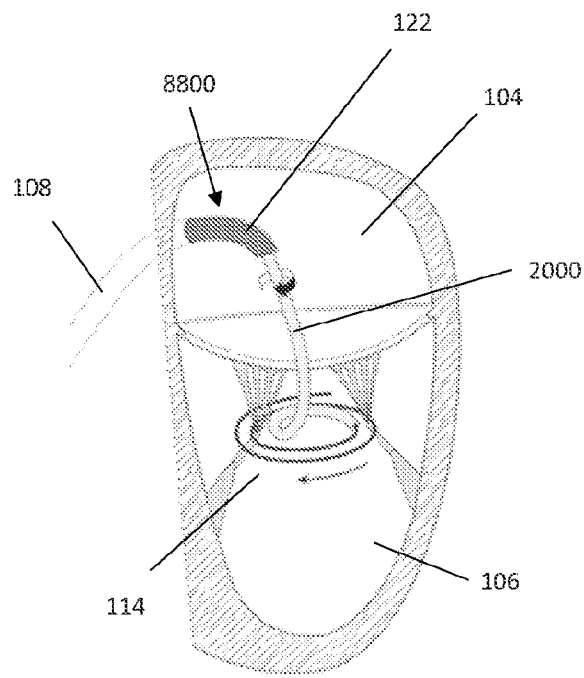
Figure 8L:
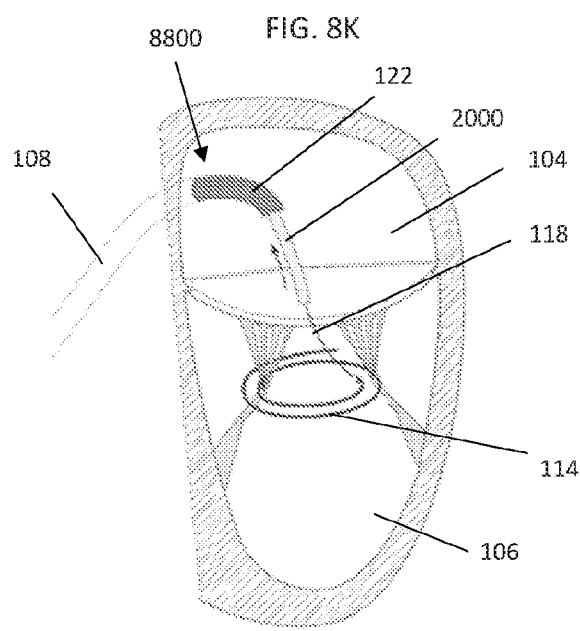
Figure 8M:
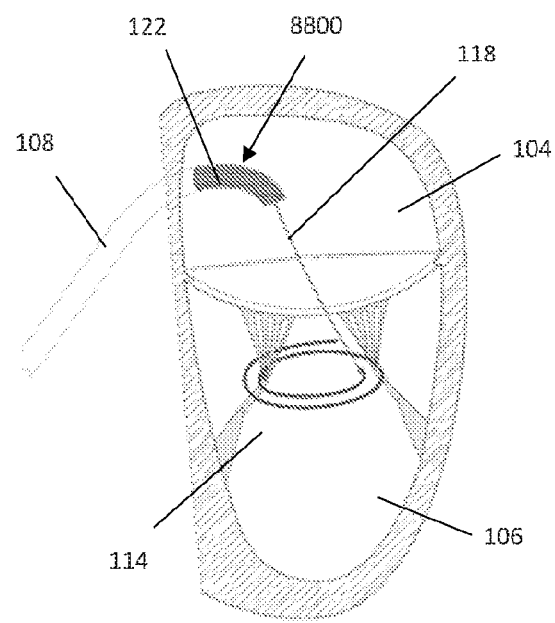

In some embodiments, the anchor guide 2000 can be part of a double catheter delivery system (e.g., a delivery system that includes a catheter for delivery of the anchor 114 and a separate catheter for delivery of the valve 120). For example, FIGS. 8A-8M show a method of delivering an anchor 114 with an anchor delivery catheter 8800 such that a valve can be delivered thereafter. At FIG. 8A, an anchor delivery catheter 8800 is tracked (e.g., over a guidewire) through a transseptal puncture into an atrium 104 of the heart, and an anchor control catheter 122 (with guide arm 2000) can begin deployment (e.g., from outer sheath 108) into the atrium 104. At FIG. 8B, the guide arm 2000 can be fully deployed from the sheath 108 into the atrium 104 and transitioned from the first configuration to the second configuration. At FIG. 8C, the anchor 114 can begin to be deployed through the lumen in the guide arm 2000 such that the flat spiral anchor 114 curves within the same plane as the distal section of the guide arm 2000. At FIG. 8D, the anchor 114 can be fully deployed within the atrium 114 such that the anchor 114 wraps concentrically about the proximal section of the guide arm 2000 (and/or the axis of the delivery catheter 8800). At FIG. 8E, the outer sheath 108 can be deflected and/or the anchor control catheter 122 can be translated distally so as to move the deployed anchor 114 towards the mitral valve annulus. At FIG. 8F, the outer sheath 108 can be steered so as to adjust the plane of the anchor 114 to be parallel to the mitral annulus. At FIG. 8G, the anchor 114 and guide 2000 can be translated distally across the mitral valve annulus. In some embodiments, the anchor guide 114 can be counter-rotated (e.g., in a direction such that the distal tip of the anchor guide 2000 trails rotation) while being translated so as to avoid entanglement with the native anatomy. At FIG. 8H, the anchor 114 and guide 2000 can be fully translated (e.g., with additional counter-rotation) into the ventricle 106. At FIG. 8I, the anchor guide 2000 can be rotated forward (starting with the distal tip near the LVOT) such that the tip of the anchor travels between the ventricular walls and the native leaflets/ chordae. At FIGS. 8J and 8K, the anchor 114 can be fully encircled via further forward rotation of the anchor guide 2000. At FIG. 8L, the anchor control catheter 122 and guide 2000 can be removed from the patient, leaving a tether 118 in position. A valve can then be delivered within the anchor 114, such as over the tether 118 (e.g., in a similar manner as described with respect to FIGS. 4G-4K).

Figure 9A:
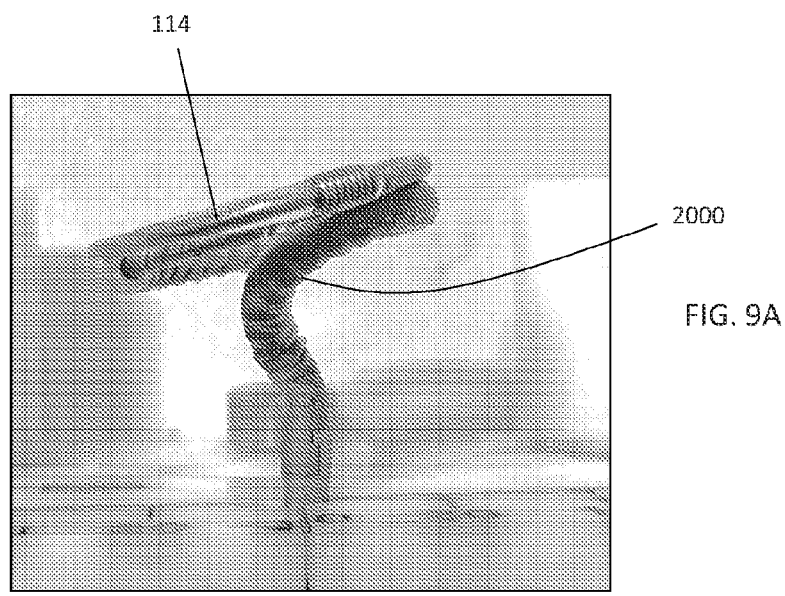
FIGS. 9A-9C show a flat spiral anchor deployed from an anchor guide similar to that shown in FIGS. 7A-7I.
Figure 9B:
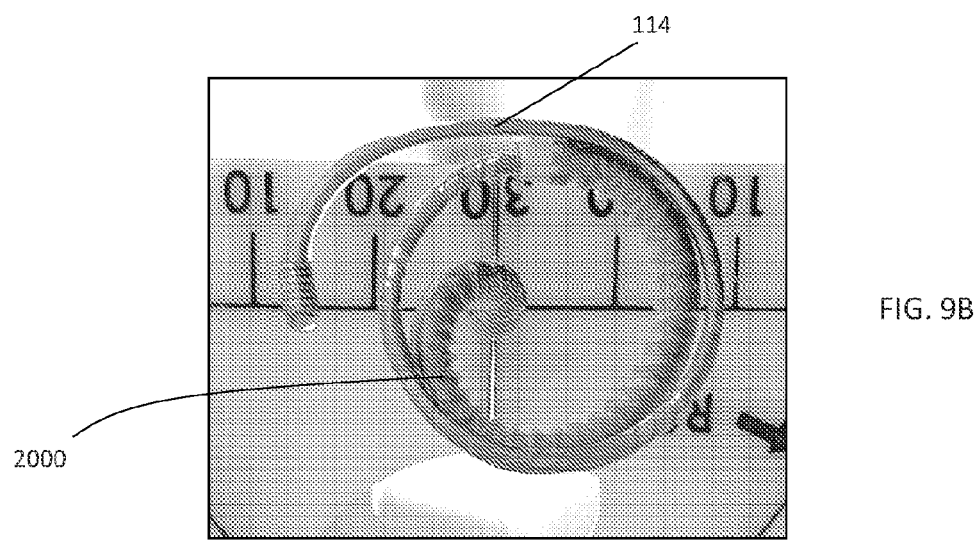
Figure 9C:
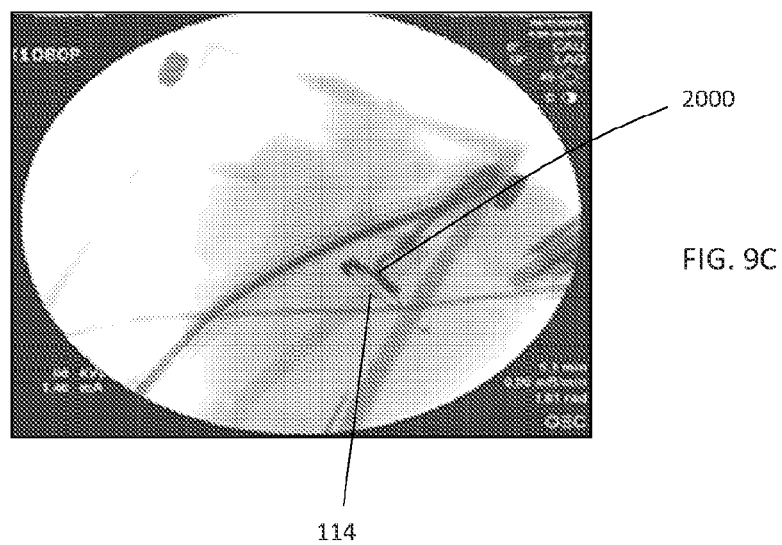

Advantageously, as shown in FIGS. 9A-9C, the distal section of the anchor guide 2000 can be configured so as to closely match both the curvature and the planarity of (e.g., at least a portion of) the flat spiral anchor 114. This configuration can enable precise placement of the anchor 114 during delivery. Additionally, the anchor guide 2000 can advantageously take up a small axial space in the heart (e.g., less than 25 mm, such as less than 22 mm, such as 21 mm or less), thereby minimizing effects on the local anatomy. The anchor guide 2000 can further advantageously be delivered to the heart via tortuous anatomy when in a flexible configuration and can then be stiffened so as to enable fine control of the anchor 114.

Referring to FIGS. 11A-11B, in some embodiments, the anchor control catheter 122 and guide 2000 can include two shafts (an inner actuation shaft 1111 and an outer torque shaft 1112) that together make up the concentric actuation mechanism. The inner actuation shaft 1111 and outer torque shaft 1112 can be bonded together at the distal end (e.g., via the interlocking teeth shown in FIG. 11A), but free to move relative to one another at the proximal end (shown in FIG. 11B). Thus, as a proximal force is applied to the inner actuation shaft 1111, the cuts in the outer torque shaft 1112 (e.g., in the anchor guide 2000) can begin to compress together, enabling the anchor guide 2000 to take on the second configuration. In some embodiments, the inner actuation shaft 1111 can be made of a tungsten coil over a liner, a braid over a coil, or a Pebax lamination. In some embodiments, the proximal portion of the outer torque shaft 1112 can be made of stainless steel while the distal portion of the outer torque shaft 1112 (making up the anchor guide 2000) can be made of nitinol. Although described herein as being actuated by a concentric actuation mechanism, it should be understood that other actuation mechanisms can be use for anchor guide 2000. For example, a plurality of pullwires can be used to actuate (as described with respect to anchor guide 1000) the anchor guide 2000. As another example, an outer sleeve can be pulled proximally relative to the anchor guide 2000 to transition the anchor guide 2000 from the first configuration to the second configuration.

Figure 12A:
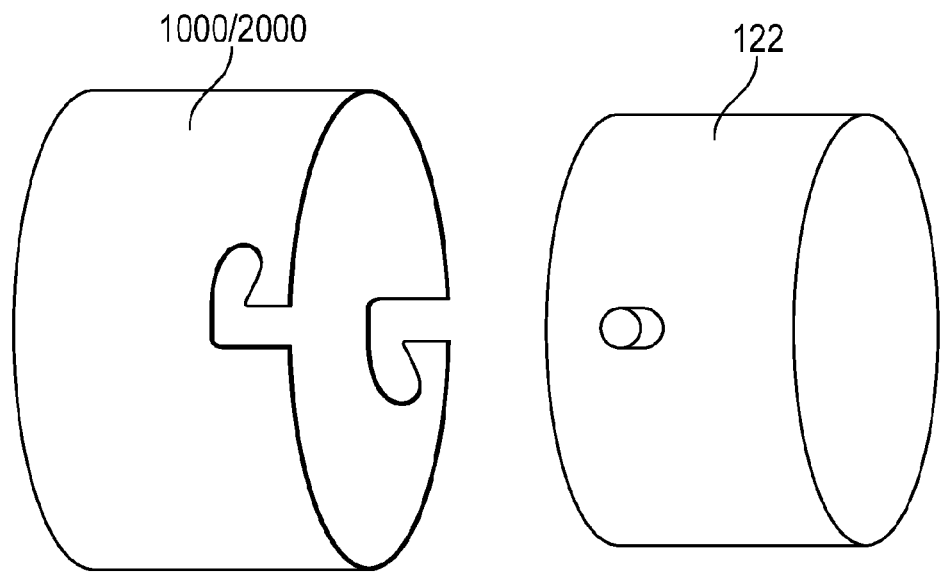
FIGS. 12A-12B show the exemplary attachment of an anchor control catheter to an anchor guide.
Figure 12B:
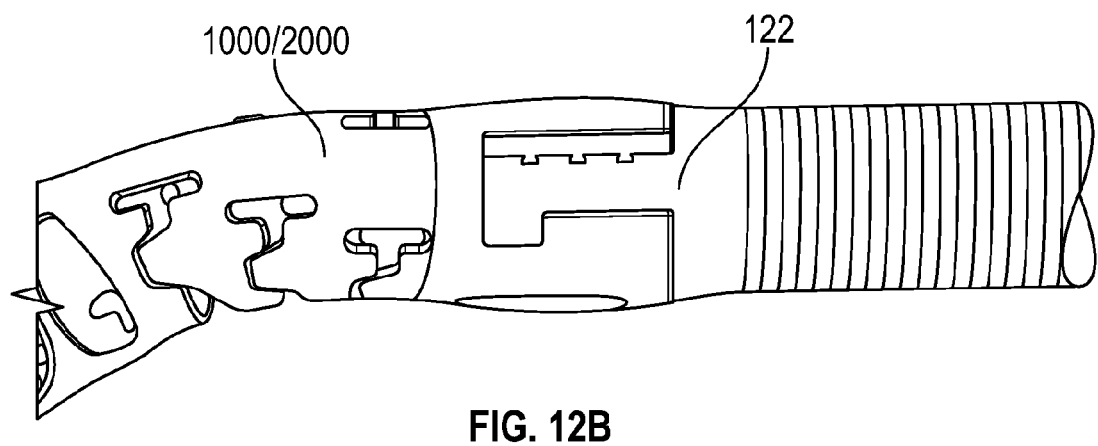

Referring to FIGS. 12A-12B, the anchor guides 1000/2000 described herein and the anchor control catheter 122 can be bonded together via interlocking features configured to transfer torque for rotation of the anchor guide 1000/2000. For example, as shown in FIG. 12A, the proximal section of the anchor guide 1000/2000 can include an L-shaped notch therein configured to interlock with a radial extension on the anchor control catheter 122. The joint can then be bonded together. As another example and as shown in FIG. 12B, the anchor guide 1000/2000 can include a notch configured to engage with a corresponding notch on the anchor control catheter 122, and the joint can then be bonded together.

Advantageously, the anchor guides 1000/2000 described herein enable the anchor 114 to be positioned concentric to the axis of rotation of the anchor control catheter 122, thereby enabling the anchor to rotate concentrically about the native chordae when the anchor control catheter 122 is rotated.

Although the anchor guides 1000/2000 are described herein as transitioning from the first to the second configuration after exiting the sheath 108 and before deployment of the anchor 114, other sequences of steps are possible. For example, in one method, the anchor 114 may be deployed from the anchor guide 1000/2000 while the anchor guide 1000/2000 is in an intermediate configuration (i.e., between the first and second configurations). For example, the anchor 114 can be deployed from the anchor guide 1000/2000 while it is in an intermediate shape set configuration. The anchor guide 1000/2000 can then be fully transitioned to the second configuration when the anchor 114 has been partially or fully deployed from the anchor guide 1000/2000. Having the anchor 114 deployed from the anchor guide 1000/2000 while the anchor guide 1000/2000 is in the intermediate shape set configuration may advantageously reduce friction on the anchor 114 as the anchor 114 moves through the anchor guide 1000/2000 while also advantageously directing the anchor 114 to wrap around the anchor guide 1000/2000 (e.g., for concentric positioning when the anchor guide 1000/2000 is in the second configuration).

Additional delivery system features are described in International Application No. PCT/US2020/023671, filed on Mar. 19, 2020, titled "PROSTHETIC CARDIAC VALVE DEVICES, SYSTEMS, AND METHODS," now PCT Publication No. WO 2020/191216 and in International Application No. PCT/US2021/040623, filed on Jul. 7, 2021, titled "VALVE DELIVERY SYSTEM," the entirety of which is incorporated by reference herein.

The anchor described herein can be a spiral anchor (e.g., a flat spiral anchor). The anchor can be configured to extend around the chordae of the valve (e.g., the mitral valve) and around the valve prosthesis to hold the valve prosthesis in place. Exemplary anchors are described in International Application No. PCT/US2019/068088, filed on Dec. 20, 2019, titled "PROSTHETIC CARDIAC VALVE DEVICES, SYSTEMS, AND METHODS," now PCT Publication No. WO 2020/132590, the entirety of which is incorporated by reference herein. In some embodiments, the anchor can have a proximal end (e.g., the end configured to engage with the delivery system) that is substantially in the plane of the annulus or is pointed down into the ventricle.

The valve prosthesis described herein can be similar to those of existing transcatheter-delivered valves. The valve prosthesis can be similar to existing surgical tissue valves, and mechanical valves. At least a portion of the valve segment may be positioned within at least a portion of the valve prosthesis, for example with a frame structure of the valve prosthesis. The valve segment may include leaflets formed of multi-layered materials for preferential function. The valve segment may comprise at least one leaflet having an inner layer and an outer layer. The valve segment may be attached directly to the valve prosthesis. Alternatively, the valve segment may be attached to an intermediate valve structure that is in turn connected to the valve prosthesis. The valve segment may be connected to the valve prosthesis before or after the valve prosthesis has been deployed adjacent a native valve. The valve prosthesis may be attached to a leaflet of the valve segment, for example an outer layer of a leaflet, at one or more ends of the valve prosthesis. The valve prosthesis may be attached to a leaflet of the valve segment, for example an outer layer of a leaflet, at one or more intermediate portions of the valve prosthesis. The valve segment may comprise a plurality of leaflets. The valve segment may comprise a biocompatible one-way valve. Flow in one direction may cause the leaflet(s) to deflect open and flow in the opposite direction may cause the leaflet(s) to close.

The frame structure may be configured like a stent. The frame structure may, for example, comprise a scaffold in a diamond pattern formed from a shape memory material (e.g., nitinol, NiTi). One of ordinary skill in the art will appreciate that many other structures, materials, and configurations may be employed for the frame structure. For example, the frame structure may be formed of a polymer of sufficient elasticity. The frame structure may be formed of a combination of metal and polymer, such as metal (e.g., shape memory material) covered in polymer. The frame structure may include a variety of patterns besides diamond shapes. In some embodiments, the frame structure is a closed frame such that blood flow is forced through valve segment therein. One or more skirts and/or seals may help force blood through the valve segment. Exemplary frame structures and valve prostheses are described in International Application No. PCT/US2020/027744, filed on Apr. 10, 2020, titled "MINIMAL FRAME PROSTHETIC CARDIAC VALVE DELIVERY DEVICES, SYSTEMS, AND METHODS," now PCT Publication No. WO 2020/210685, the entirety of which is incorporated by reference herein.

One of ordinary skill in the art will recognize based on the description herein that any of the valve prostheses described herein may comprise any of the frame structure shapes, frame structure designs, frame structure materials, anchor shapes, anchor windings, anchor materials, free end tips, leaflet(s) configurations, or any other of the variable features described herein in any combination thereof as desired.

It should be understood that any feature described herein with respect to one embodiment may be combined with or substituted for any feature described with respect to another embodiment.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected," "attached" or "coupled" to another feature or element, it can be directly connected, attached or coupled to the other feature or element or intervening features or elements may be present. In contrast, when a feature or element is referred to as being "directly connected," "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise," and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), or +/−10% of the stated value (or range of values). Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that these data represent endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A delivery system for delivering a spiral an anchor to a diseased native valve of a heart, comprising:
   an anchor control catheter; and
   an anchor guide extending from the anchor control catheter, the anchor guide comprising a flexible configuration with an elongate delivery geometry and a rigid configuration with a curved deployed geometry, the anchor guide in the rigid configuration comprises a proximal section, a middle section, and a distal section, wherein the proximal section comprises a straight central axis and extends from the anchor control catheter, the middle section spirals axially and radially outwards from the straight central axis, and the distal section curves concentrically about the straight central axis in a plane that is perpendicular to the straight central axis, wherein the anchor guide is shape-set to assume an intermediate configuration that has an intermediate geometry that is between the elongate delivery geometry and the curved deployed geometry.

2. The delivery system of claim 1, wherein the anchor guide comprises a plurality of cuts configured to define a shape of the anchor guide in the rigid configuration.

3. The delivery system of claim 2, wherein the plurality of cuts comprises window cuts, interlocking spiral cuts, or toothed wedge cuts.

4. The delivery system of claim 1, further comprising one or more actuation elements configured to actuate the anchor guide from the flexible configuration to the rigid configuration.

5. The delivery system of claim 4, wherein the one or more actuation elements comprises a nested concentric shaft mechanism or one or more pullwires or cables.

6. The delivery system of claim 1, wherein the anchor guide comprises a shape memory material.

7. The delivery system of claim 1, wherein the anchor guide comprises a central channel configured to hold the anchor therein.

8. The delivery system of claim 7, wherein the anchor guide is configured to deflect the anchor positioned within the central channel when the anchor guide is transitioned from the flexible configuration to the rigid configuration.

9. The delivery system of claim 8, wherein the anchor guide is configured to position the anchor concentrically relative to a central axis of the anchor control catheter.

10. The delivery system of claim 1, wherein the anchor guide in the flexible configuration is configured to be positioned within a delivery sheath.

* * * * *